United States Patent [19]

Bechtel et al.

[11] Patent Number: 4,972,154

[45] Date of Patent: Nov. 20, 1990

[54] APPARATUS AND METHOD FOR MEASURING WOOD GRAIN ANGLE

[75] Inventors: Friend K. Bechtel, Moscow, Id.; James R. Allen; James D. Logan, both of Pullman, Wash.

[73] Assignee: Metriguard, Inc, Pullman, Wash.

[21] Appl. No.: 362,956

[22] Filed: Jun. 6, 1989

[51] Int. Cl.⁵ .......................................... G01R 27/26
[52] U.S. Cl. ................................... 324/663; 324/688; 324/690
[58] Field of Search ............... 324/663, 686, 687, 688, 324/690

[56] References Cited

U.S. PATENT DOCUMENTS

| | | | |
|---|---|---|---|
| 3,515,987 | 6/1970 | Zurbrick et al. | 324/687 |
| 3,805,156 | 4/1974 | Norton et al. | 324/61 R |
| 4,007,454 | 2/1977 | Cain et al. | 340/200 |
| 4,433,332 | 2/1984 | Wason | 324/660 |

OTHER PUBLICATIONS

James, W. L., 1975, "Dielectric Properties of Wood & Hardboard: Variations with Temperature, Frequency, Moisture Content, and Grain Direction", USDA Forest Service Research Paper FPL 245, Madison, Wis.

Bechtel, F. K. and Allen, J. R., "Methods of Implementing Grain Angle Measurements in the Machine Stress Rating Process", Sixth Nondestructive Testing of Wood Symposium, Washington State University, Pullman, Wash., Sep. 1987.

Metriguard, Inc., Product Brochure-Grain Angle.

*Primary Examiner*—Reinhard J. Eisenzopf
*Assistant Examiner*—Maura K. Regan
*Attorney, Agent, or Firm*—Wells, St. John & Roberts

[57] ABSTRACT

Wood grain angle information is detected electronically by use of a sensor having a common electrode and a plurality of electrodes spaced from the common electrode and arranged angularly about a sensor axis. The common electrode can serve as a sense electrode or as a drive electrode for the remaining angularly spaced electrodes. By modulating applied drive signals and demodulating the sensed signals that result from capacitive coupling of an adjacent wood specimen, values that are a function of wood grain angle are identified.

49 Claims, 13 Drawing Sheets

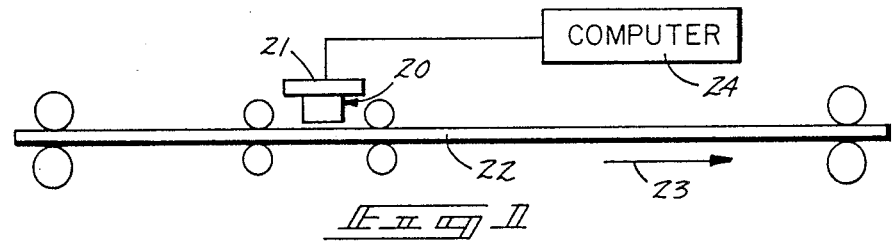
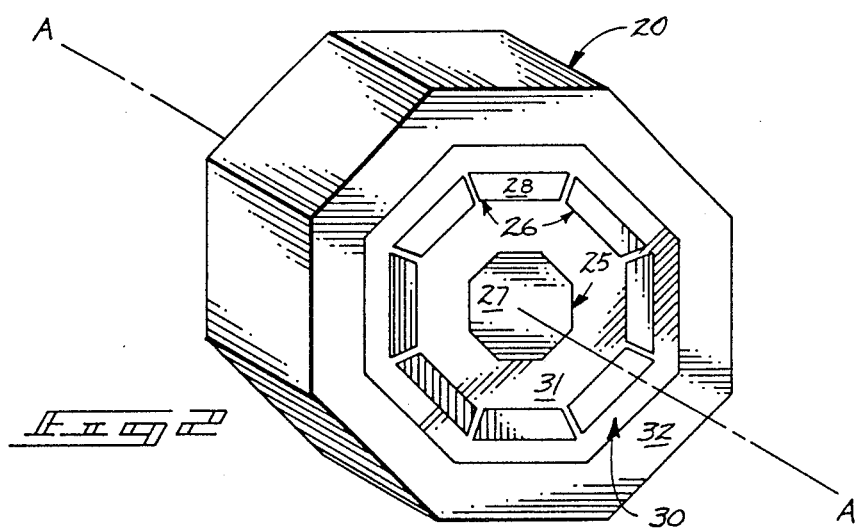
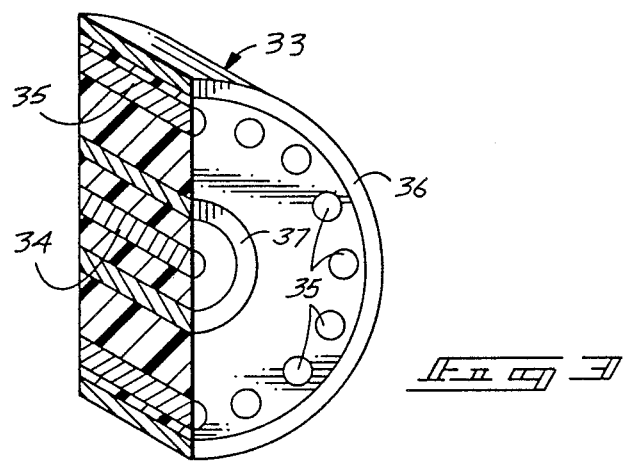

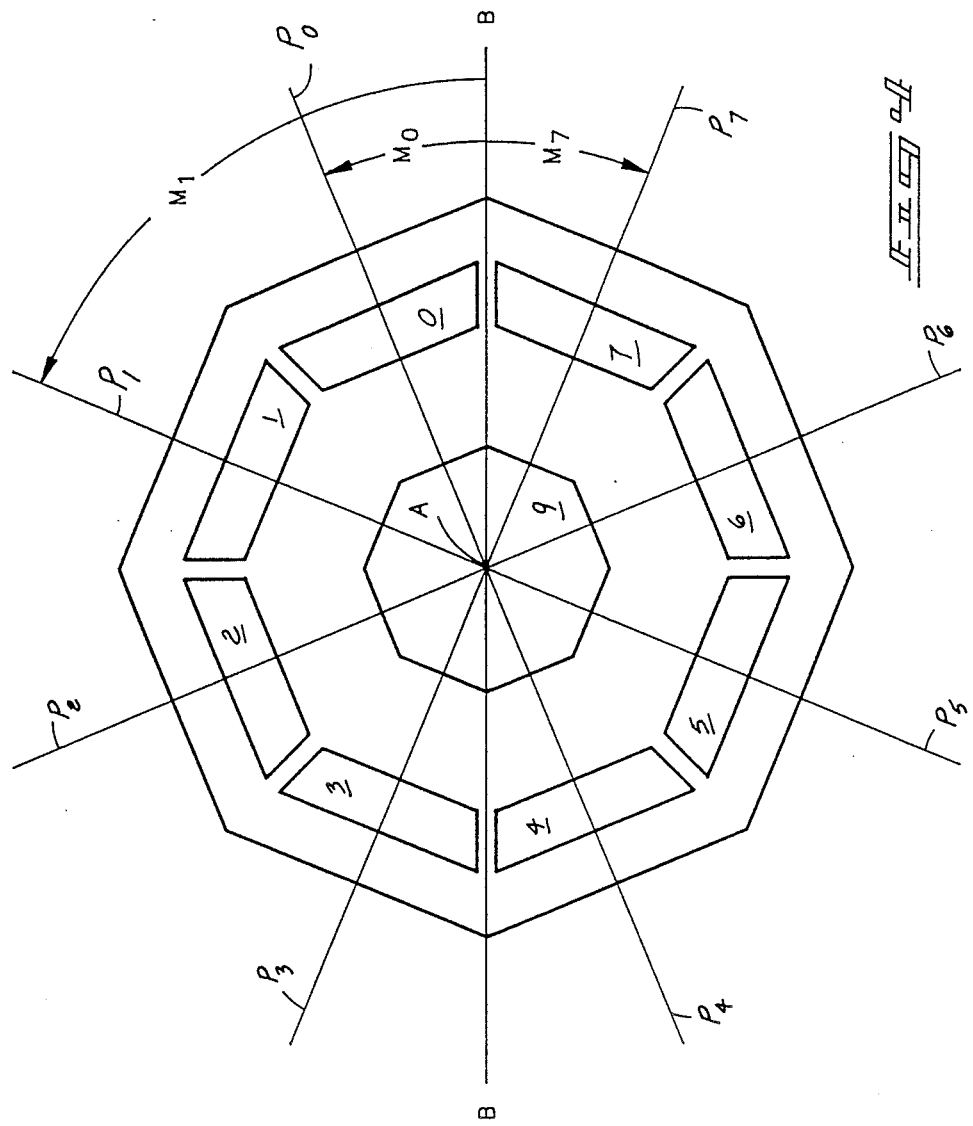

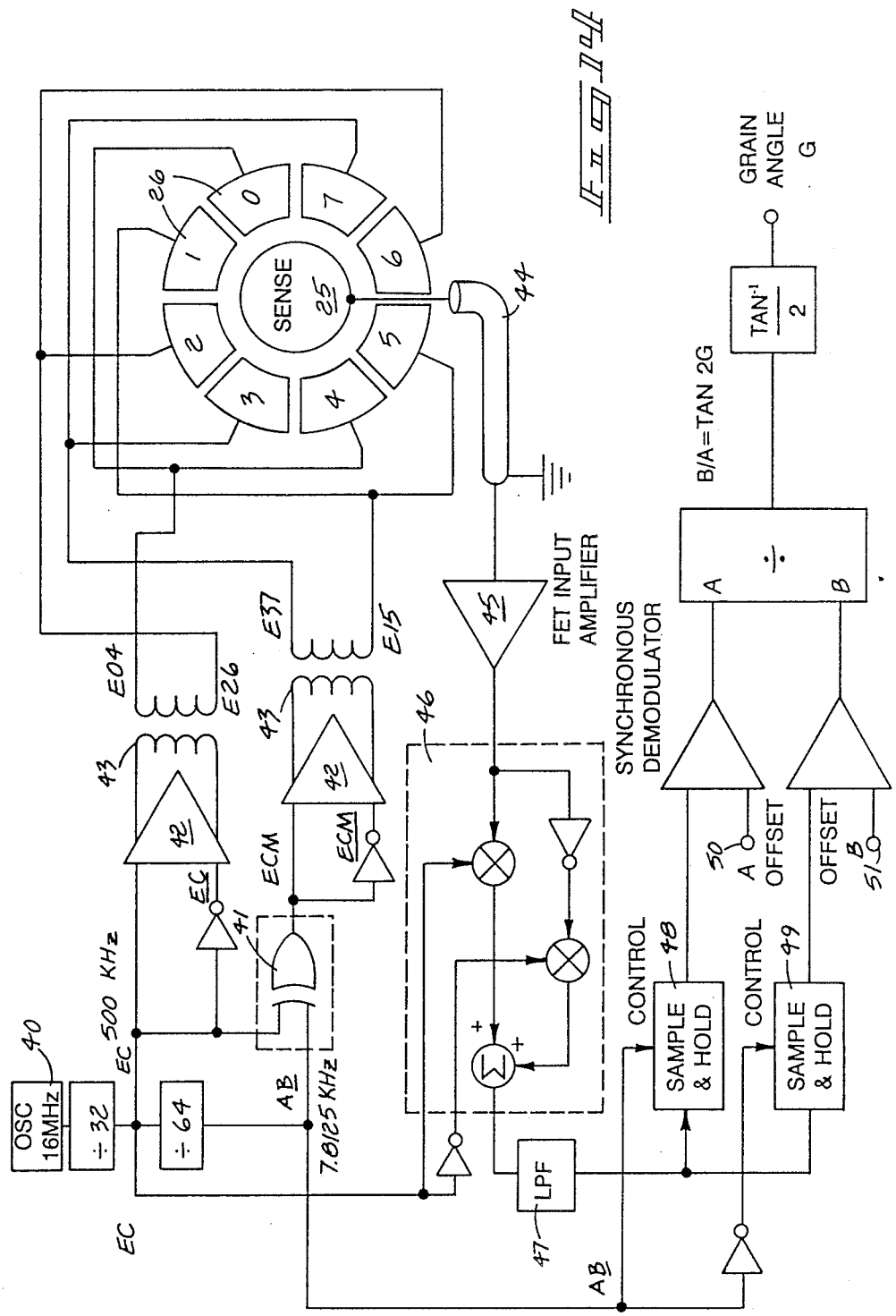

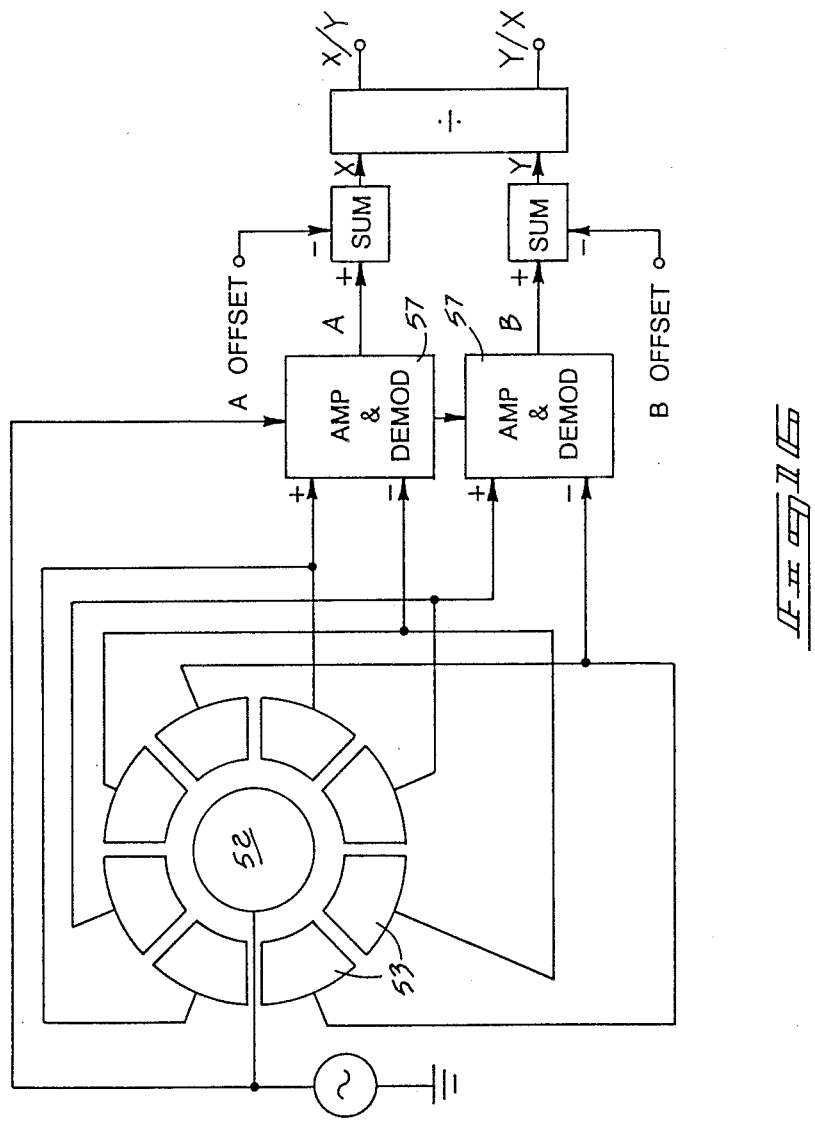

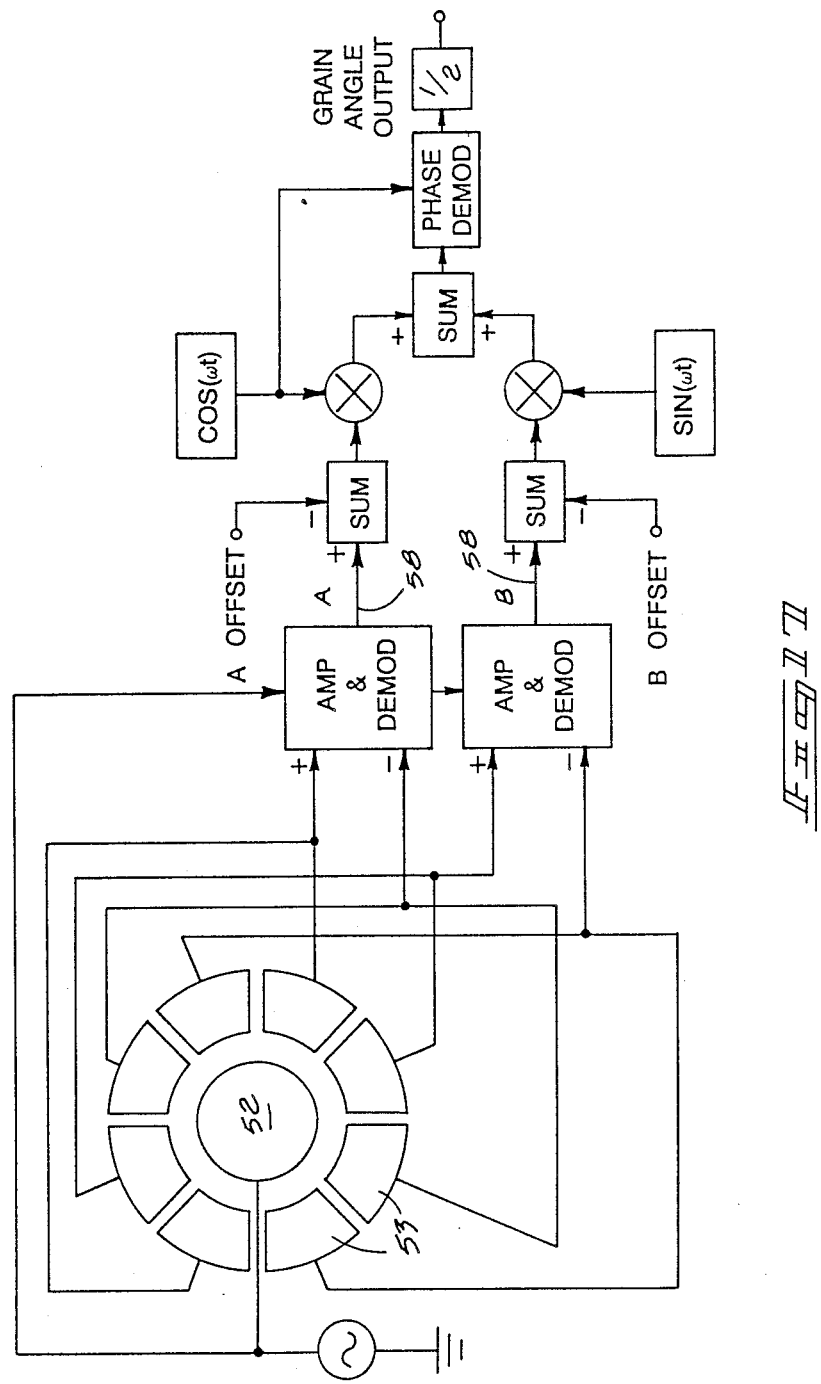

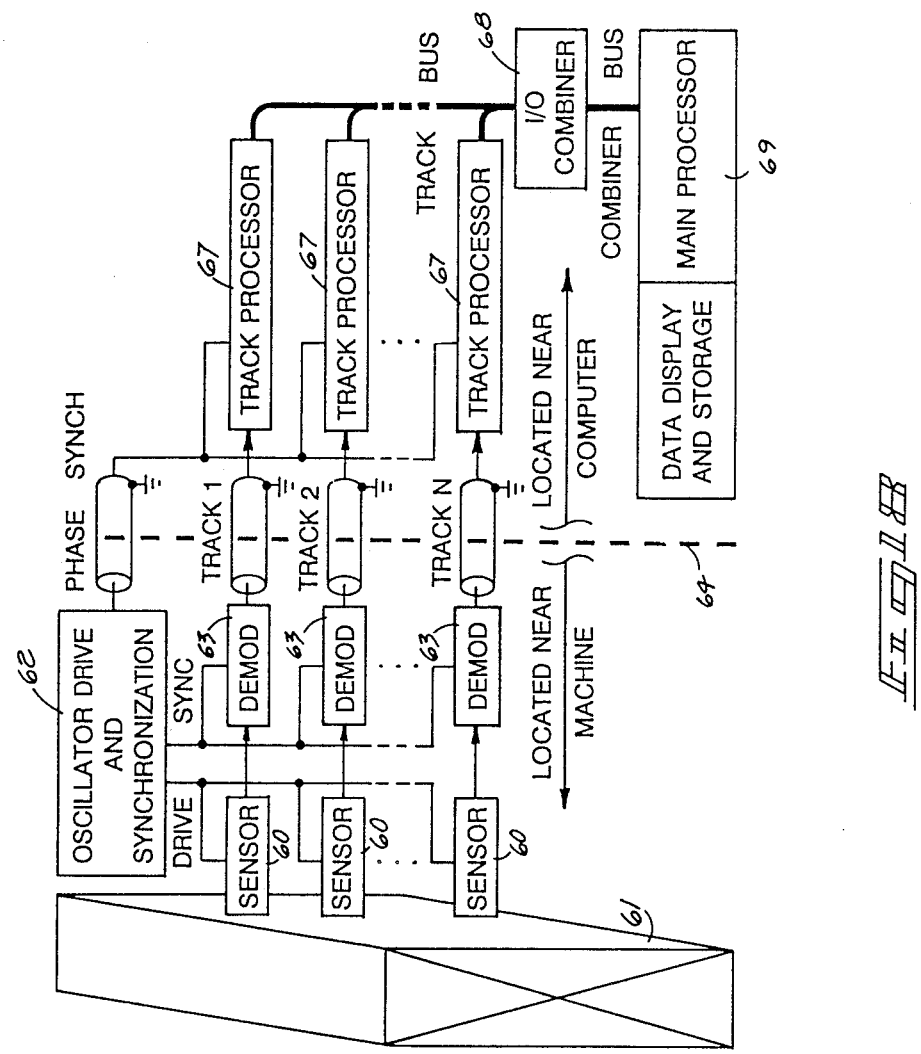

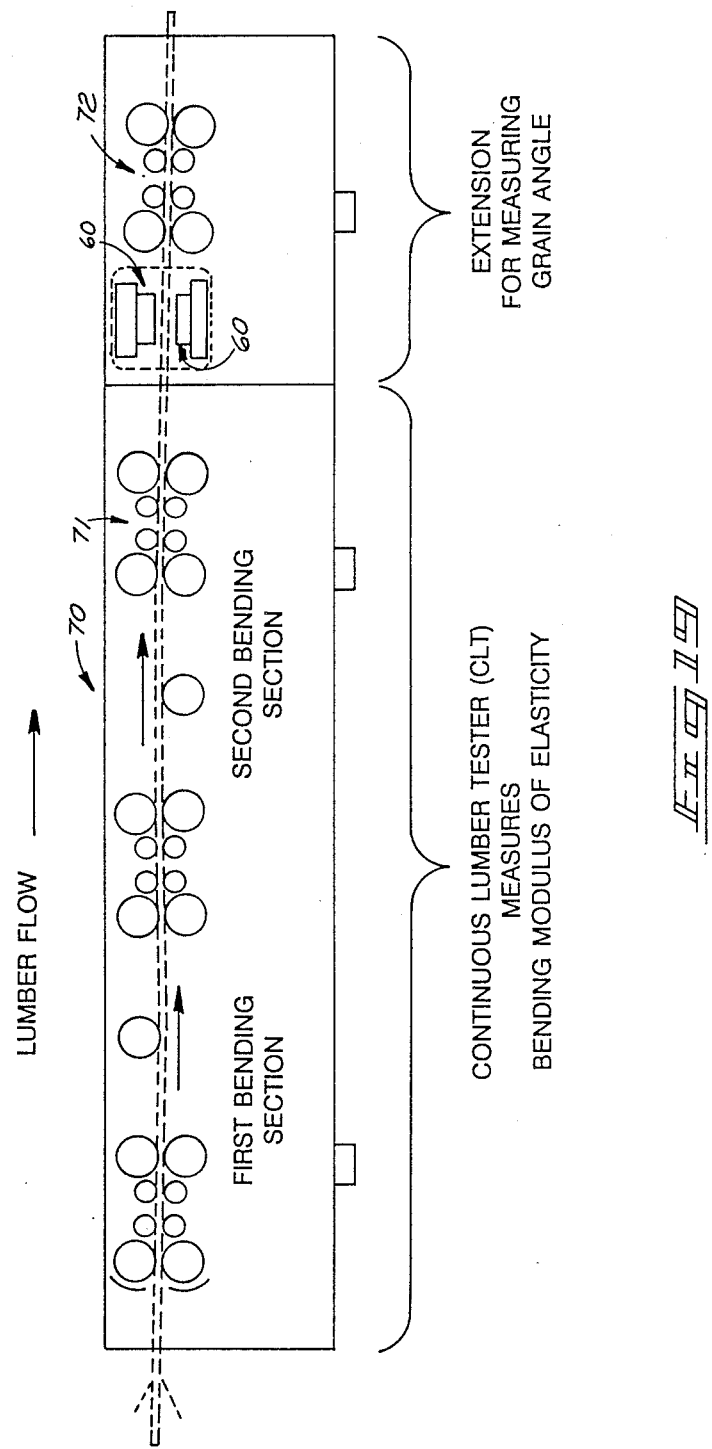

APPARATUS AND METHOD FOR MEASURING WOOD GRAIN ANGLE

TECHNICAL FIELD

This disclosure pertains to equipment and methods for quantifying or measuring wood grain angle in lumber specimens or other wood products.

BACKGROUND OF THE INVENTION

Importance of Grain Angle

Grain angle measurements are important in the estimation of tensile strength of lumber. Accurate nondestructive estimates of tensile strength are presently needed in the machine-stress-rating process for dimension lumber. Improved strength estimation will allow the industry to more fully utilize the structural value of lumber and hence the forest resource. Also, better knowledge of lumber strength will allow lumber to compete more effectively with other structural materials, such as steel and concrete. The research that led to the present invention was intended to prove the feasibility of increased grain angle measurement speed capability so that measurements and subsequent strength estimation could be performed at production speeds.

Present Equipment

The currently-available and successful low speed mechanically rotating sensor concept for measurement of grain angle has been used mainly for laboratory and research purposes. Details of such equipment are found in Norton et al., U.S. Pat. No. 3,805,156 (Canadian Patent No. 943,187) and in machines designated as the Metriguard Models 5100 and 510, produced by Metriguard, Inc. of Pullman, Wash. U.S.A.

Prior Art

It is well known that the dielectric permittivity of wood is a function of wood fiber direction relative to the direction of an applied radio frequency measurement field with maximum permittivity occurring along the direction of the fibers (James, W. L., 1975. Dielectric properties of wood & hardboard: variations with temperature, frequency, moisture content, and grain direction. USDA Forest service Research Paper FPL 245. Madison, Wis.). The Norton et al. patent and present equipment utilize this anisotropy by means of mechanically rotating capacitor electrodes with operative surfaces placed near the wood to be measured. As the electrodes rotate relative to the wood fiber direction, the capacitance between them changes as a function of the changing permittivity. The phase of the electrical signal developed from the varying capacitance is used to obtain grain angle.

As well as mechanical rotation for the capacitor electrodes, the above patent discloses a method using stationary capacitor electrodes to generate an electronically rotating field. This method would utilize capacitor electrodes in diagonally opposite pairs. It is clear from the disclosure, that the intent is to obtain a capacitance value between opposite electrodes in a diagonally opposite pair of electrodes as though they had been rotated at a uniform rotational speed.

Present Requirements

The as yet unfilled need for accurate, real-time estimation of lumber strength has led to a requirement for accurate high speed grain angle measuring equipment, grain angle having been shown to be valuable in the estimation of lumber tensile strength. The grain angle measurement process must keep up with lumber production speeds of approximately 1400 lineal feet/min (427 meters/min).

Additionally, a requirement exists for portable hand-held equipment suitable for measuring wood grain angle in timber structures and for spot checking or quality control of wood product manufacturing.

Grain angle measuring equipment will also be useful in defect detection and control processes where, for example, saws would be used to automatically cut out defects such as knots or burls which show up in wood as local areas of grain angle deviations.

Limitations of Present Implementations

The presently implemented prior art consists of equipment utilizing mechanically rotating capacitor electrode sensors. This equipment has proved accurate and useful in the laboratory; but its useful speed capability is presently limited to about 200 feet/min (61 meters/min), this being the speed of lumber moving past the sensor. The measurement speed capability is directly proportional to the mechanical rotation speed of the sensors. There are known problems with increasing the rotational speed. The mechanically rotating sensors contain electronic components; increasing speed subjects these components to increasing mechanical stresses and reduced reliability. Signals are brought into and taken out of the rotating sensor via slip rings. Slip ring induced electrical noise, wear, and reliability are problems that become more severe with increasing speed and these are problems already encountered to some extent with the present equipment operating at the present rotation speeds. Production measurement speeds would require sensor rotation speeds well beyond practical slip ring capabilities.

Limitations of Prior Art

The mechanical rotation concept could be pushed to speeds somewhat higher than presently implemented, but that approach is subject to problems as pointed out above and in the Norton et al. patent.

The method disclosed by Norton et al. for using stationary capacitor electrodes to generate an electronically rotating field depends on capacitance transducers that are capable of producing a voltage signal proportional to capacitance. The capacitance transducers are an integral part of the system.

In the process of developing the presently available mechanical rotation grain angle measuring equipment, we discovered that development of capacitance transducers capable of measuring tiny capacitance values and their variation with wood grain angle in the presence of perturbing parameters such as stray circuit capacitance is not a trivial problem. In fact, the development sequence involved three different approaches, each utilizing basically different capacitance transducer concepts before the present satisfactory implementation for the mechanically rotating sensor was achieved.

We are not aware of any similar development and implementation utilizing a stationary sensor. The same difficulties regarding measurement of tiny capacitance values in the presence of perturbing parameters exist for the stationary sensor as for the mechanically rotating sensor. In addition a means other than mechanical rotation must be invoked for investigating capacitance in the different directions. An analysis of the Norton et al. proposed stationary grain angle measurement method shows that in principle it could achieve by electronic means a rotating capacitance measurement effect with pairs of spaced electrodes. However, their proposed method involves looking at electrodes in spaced pairs. Their electrode arrangement and capacitance transducer method for obtaining voltages proportional to capacitance has practical limitations when measuring tiny capacitances in the presence of larger circuit stray capacitances. We have found this problem to be a key practical limitation of the prior art when the capacitances are small and stray circuit capacitances are present as they must be by nature of connections to the pairs of electrodes. Also, the Norton et al. proposed physical geometric arrangement of diagonally opposite pairs of spaced electrodes necessarily limits the capacitance between the two members of each pair of spaced electrodes. This aggravates the problem where stray circuit capacitances can be large with respect to the electrode pair capacitances. This is clear from a calculation of capacitance between two electrodes, which shows that the capacitance is inversely proportional to the distance between them and proportional to their effective areas. In the case of the Norton et al. proposed arrangement of diagonally opposite electrode pairs, the electrode areas near each other are necessarily small for each pair of electrodes. Hence the capacitance is small.

In our first attempt at implementing a stationary sensor concept for grain angle measurements, we discovered another difficulty. Our successful efforts with the mechanically rotating sensor led us to implement an electronic rotation by electrically switching connections to an array of capacitor electrodes with geometry similar to the array described by Norton et al. The switched connections grouped electrodes together in a rotational sequence so that at any moment the electrode groups each appeared as a single electrode similar to an electrode of the mechanically rotating sensor at a particular moment in its rotation. During the next phase of the switching sequence, the connected groups appear as electrodes of the mechanically rotating sensor in a position rotationally advanced from the previous position. By connecting electrodes in this way, the capacitances measured were capacitances between adjacent electrode groups and not between diagonally opposite pairs of electrodes and hence were larger than capacitances of diagonally opposite pairs. However, we encountered practical difficulties with switching individual electrodes between drive and sensing circuitry as was required for this approach. The approach used the measurements obtained at each phase as samples of capacitance in directions at discrete rotational increments. These capacitance values can be processed to obtain the grain angle. As part of this effort, we developed a method for learning the stray capacitances and subtracting them from the signal.

Both the Norton et al. method and the switched electrode method show some promise for measuring grain angle; however, the practical difficulties encountered led us to explore other ideas and led to the present invention.

Summary of the New Invention

Our efforts to increase the speed of wood grain angle measurements with a practical stationary system led to the discovery of a new capacitor electrode array sensor geometry and new methods utilizing this geometry for measuring wood grain angle. Sensitivities of the new approach to rate of change of grain angle (speed), wood-to-sensor spacing, lack of parallelness between sensor and wood surfaces, sensor size, and effect of pitch buildup were explored, and the approach found to have practical application in the wood products industry.

Tests simulating lumber speeds considerably in excess of current fastest production-line machine stress rating speeds of 1400 ft/min (427 meters/min) proved grain angle measurement accuracy of 1 degree in the domain from −30 to +30 degrees for the new sensor. Variations we disclose allow accurate grain angle measurements from −90 to +90 degrees. The speed and sensitivity tests prove that grain angle measurement at production speeds is feasible. Analysis of additional test data verified the value of these grain angle measurements in a previously derived strength estimation algorithm.

These discoveries are expected to lead to industry implementation of production-line grain angle measurements, along with better strength estimation in the machine stress rating process. Another application made possible by the present disclosure is a practical hand-held grain angle measuring instrument for spot checks by lumber graders, researchers, and building inspectors. Still another application is the control of equipment for removing defects in wood products.

The following list of accomplishments summarizes key aspects of a particular embodiment of our invention and our proof of the feasibility of accurate high speed grain angle measurements using the new invention.

1. We discovered a new capacitor electrode array sensor geometry that has some inherent preprocessing advantages and a new grain angle measurement processing method utilizing the new sensor geometry which allows accurate grain angle measurements. This method is particularly well suited to our overall goal of tensile strength estimation. The "tracks" model used in our tensile strength estimation algorithm has been shown to perform well when angles outside +/−25 degrees are lumped into one "bad" category, and the new approach can be simplified even further to take advantage of this fact. (Bechtel, F. K. and Allen, J. R. "Methods of Implementing Grain Angle Measurements in the Machine Stress Rating Process," Sixth Nondestructive Testing of Wood Symposium, Washington State University, Pullman, Wash., September 1987.)

2. Capacitor electrode array sensors and processing circuitry were constructed to test feasibility of the ideas. Lineal speed capability was tested at simulated lumber speeds of 1216 ft/min (371 m/min) and 1951 ft/min (595 m/min), where simulation was achieved by rotating a wood test block adjacent to the sensor. No decrease in grain angle measurement accuracy was observed at these speeds. This proves the high speed capability of the new approach. The simulated speed of 1951 ft/min (595 m/min) is approximately ten times the 200 ft/min (61 m/min) speed capability for the present mechanically rotating sensors.

3. Three different sensor sizes were investigated. The largest exhibited accurate grain angle measurement capability for wood-to-sensor distances exceeding 0.5 inch (1.27 cm).

4. Accurate grain angle measurements were made for wood-to-sensor distances of as much as 0.25 inch (0.64 cm) for the sensor size believed best suited for production-line tensile strength estimation (1.0 inch (2.54 cm) diameter). This indicates the new sensor concept should work in a production environment where lumber to sensor distance cannot always be precisely maintained.
5. We studied the sensitivity of grain angle measurement accuracy to deviations from parallel between the wood and sensor surfaces The results showed the desirability of maintaining the surfaces parallel, but the measurements were usable for small deviations from parallel. Depending on details of physical implementation, small deviations from parallel may occur in a production line.
6. We learned that pine pitch surface contamination on the sensor can distort the measurement. We demonstrated that measuring the distortion and subtracting it from the signals removes most of the effect.
7. A generic theoretical analysis was completed for a new family of sensor geometries, for methods for electrically driving the electrodes, and for methods for sensing and processing the resulting signals. This analysis allows use of probing frequencies and waveforms other than the ones tested and opens the possibility of much higher measurement speeds should they prove necessary for specific applications.

BRIEF DESCRIPTION OF THE DRAWINGS

The preferred embodiment of the invention is illustrated in the accompanying drawings, in which:

FIG. 1 is a schematic view of the equipment for measuring grain angle in lumber;

FIG. 2 is an enlarged oblique view showing the face of the sensor;

FIG. 3 is a sectioned oblique view of a second embodiment of the sensor;

FIG. 4 is a schematic plan view of the sensor face as shown in FIG. 2;

FIG. 14 is a schematic circuit diagram of a first embodiment of the driving and sensing circuit;

FIG. 15 is a schematic circuit diagram showing reversal of the driving and sensing functions in the sensor electrodes;

FIG. 16 is a second schematic circuit diagram showing alternative processing;

FIG. 17 is a third schematic circuit diagram showing other alternative processing;

FIG. 18 is a schematic diagram showing application of the equipment to an existing process for tensile strength estimation; and FIG. 19 is a schematic view of production-line equipment adapted for grain angle measurement and tensile strength estimation purposes.

DETAILED DESCRIPTION OF THE PREFERRED EMBODIMENTS

Figure 5:
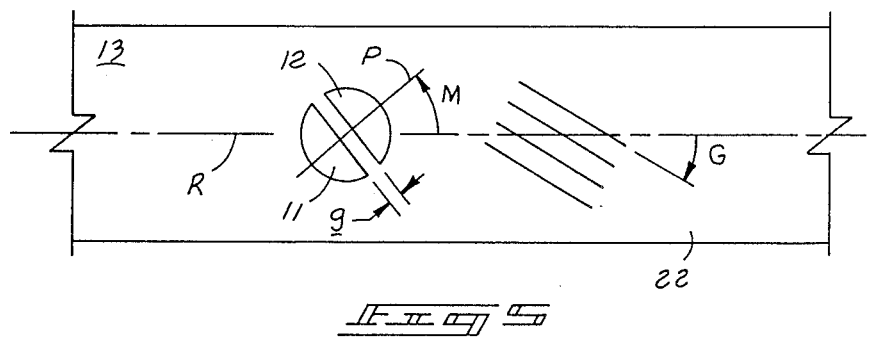
FIG. 5 is a schematic plan view diagrammatically illustrating the relationship between electrode probing direction and grain angle in a wood specimen.

The following disclosure of the invention is submitted in compliance with the constitutional purpose of the Patent Laws "to promote the progress of science and useful arts" (Article 1, Section 8).

Sensor Details

The present disclosure is based upon the discovery of a new sensor 20 (FIG. 2) for measurement of grain angle in lumber or other wood products. The sensor 20 (a second sensor configuration is shown at 33 in FIG. 3) embodies a new capacitor electrode array geometry that inherently overcomes difficulties previously observed in current equipment pertaining to wood grain angle measurement.

FIG. 1 schematically illustrates the environment in which the sensor 20 is used. The sensor 20 is supported by a bracket 21 alongside a conveyor that imparts longitudinal movement to a board 22 in the direction of arrow 23. Electrical signals received from sensor 20 are directed to a computer 24 for processing purposes.

The purpose of sensor 20 is to quantify wood grain angle values in dimension lumber or other wood materials, exemplified by board 22. It accomplishes this purpose by "scanning" a surface of board 22, using radio frequency signals. This results in capacitive coupling through the adjacent wood material. The resulting sensed signals are amplitude modulated as a function of the wood grain angle, the amount of anisotropy in the wood specimen at the vicinity of each test point, and confounding parameters such as the spacing distance from the wood sample to the sensor.

The sensor 20 has been developed for measuring wood grain angle values in lumber moving past sensor 20 at normal production facility speed. However, when desired, the sensor can be used for testing stationary boards or other wood materials, and the physical support provided to the sensor 20 can be either stationary or portable.

The sensor 20 will normally be supported in a stationary position as lumber or other wood-based products are moved past it. This simplifies sensor construction and eliminates the need for movable electrical connectors or slip rings leading to the sensor. However the sensor 20 can be mounted to move about a specimen being tested and can be rotated where this is desirable in connection with a specific grain angle measurement application.

In general, the sensor 20 includes electrically conductive first and second electrode means for effecting capacitive coupling between them through an adjacent wood specimen to detect signals that are a function of grain angle of the wood specimen. The novel physical or geometrical aspect of sensor 20 is that the first electrode means includes a common first electrode operative surface at a sensor axis A-A and the second electrode means includes a plurality of second electrode operative surfaces angularly arranged about the sensor axis.

In the present apparatus, one of the electrode means serves in the driving capacity and the remaining electrode means serves in the sensing capacity. In other words, the sensor 20 includes a dedicated common electrode that is a driving element or a sensing element at all times during use of the sensor. Capacitively coupled through the wood to this first electrode means are a plurality of angularly spaced second electrodes that serve at all times in the complementary functional capacity. This arrangement of electrodes permits use of direct wired connections to them. It allows well-defined, practical means for utilizing the capacitances between first and second electrodes in the determination of grain angle, including some inherent preprocessing that can occur as a consequence of the geometry. It eliminates the necessity of physically rotating electrodes in the sensor to obtain wood grain angle measurements as has been required with previous equipment of this type. It also eliminates the practical difficulties that result from switching electrical connections to the electrodes. In addition, capacitances between the common first electrode and the second electrodes in the geometry of the new apparatus are larger as a consequence of the described geometry than are capacitances between electrodes of pairs for the diagonally opposite pairs discussed in the Norton et al. patent.

FIG. 2 shows a first physical embodiment of the sensor 20. In this form of the invention, the first electrode means is illustrated by a flat plate electrode 25, which serves as a sense electrode. It is encircled by the second electrode means, illustrated by a plurality of flat plate electrodes 26, that serve as drive electrodes. Electrode 25 has a planar exposed operative surface 27 having an octagonal periphery. Electrodes 26 have complementary trapezoidal operative surfaces 28 lying in the plane common to surface 27, which shall be termed the "reference surface" of the sensor 20. While the surfaces 27, 28 are shown as being in a common plane, they can also be located in different planes where, as an example, different gaps are desired between the sense electrode and driving electrodes. In addition, the surfaces 27, 28 need not always be planar or of any particular shape. They can be concave, convex, bent or inclined, as examples, and can include points lying within one or more planes essentially parallel to the face of sensor 20.

The sensor 20 shown in FIG. 2 is the physical embodiment of the invention which has been primarily tested to date. In the sensors that have been constructed and used for test purposes, the width across the flat side edges of the octagonal electrode 25 has been either 0.5 inch (1.27 cm) or 1.0 inch (2.54 cm). The width across the outer flat surfaces of diametrically opposed electrodes 26 has been either 1.25 inches (3.18 cm) or 2.5 inches (6.35 cm). The gap between electrodes 25 and 26 has been either 0.125 inch (0.318 cm) or 0.25 inch (0.635 cm).

The electrodes 25 and 26 are radially spaced from one another, enabling them to be capacitively coupled through adjacent wood material. Any suitable dielectric, including air, can be used to separate the electrodes. However, because of the contamination problems encountered in wood production facilities where the sensor 20 is used closely adjacent to moving board surfaces, it is advisable to imbed the electrodes 25 and 26 within a supporting mass of dielectric material, shown at 30. The dielectric 30 can be any suitable resin or other substance capable of insulating the electrodes 25 and 26 with respect to one another and maintaining a constant physical structure in the sensor 20. Dielectric 30 might also be used to shape the fields created by electrodes 25 and 26. The dielectric 30 in the embodiment of FIG. 2 includes an outer exposed surface 31 that is almost flush with the electrode surfaces 27 and 28 and lies just below the previously identified reference surface for sensor 20. The sensors used in our experiments were printed circuit boards fabricated using standard printed circuit technology.

The illustrated sensor 20 is completed by a surrounding concentric guard ring 32 of metal or other electrically conductive material centered about the sensor axis and positioned radially outward from the second electrode means, which is shown in the form of multiple drive electrodes 26. Guard ring 32 is normally maintained at ground potential. It contains and isolates the field created by the first and second electrode means. This reduces stray adjacent electrical fields from interfering with the desired wood grain angle measurement functions of sensor 20.

When desired, a concentric guard ring can be provided between the first electrode means and second electrode means, as shown in the embodiment illustrated in FIG. 3. FIG. 3 illustrates an alternate form of sensor 33 wherein the first electrode means is a cylindrical rod 34 and the second electrode means are also cylindrical rods 35 centered equiangularly about a concentric circular path centered on the sensor axis. In addition to the outer guard ring 36, sensor 33 is provided with an intermediate guard ring 37 positioned between the first electrode means 34 and second electrode means 35. The normally grounded connection of ring 37 capacitively isolates the electrodes 34 and 35 in the neighborhood of the sensor's reference surface, assuring that the capacitive coupling that results between them is substantially achieved through the adjacent wood material being tested and not so much from sensor surface contamination by other dielectric material, such as pitch.

It will be clear that there are many geometric variations available in the design of wood grain angle sensors according to the general description previously given. As shown, the sensor 20 includes eight drive electrodes 26 and one sense electrode 25. Their functions are reversible, as described below, so that electrodes 26 can serve as multiple sense electrodes while electrode 25 serves as a common drive electrode. The use of eight electrodes 26 in the electrode array equiangularly positions the electrodes at angular spacings of 45 degrees relative to the center of electrode 25. This angular spacing is of particular functional importance in one processing application of the resulting sense signals, but can be modified to meet other processing requirements.

The number of electrodes surrounding the single electrode will depend upon the requirements of the processing techniques to be used with the sensor, but to some extent can be selected arbitrarily as will be seen from the general theoretical description. While eight electrodes 26 are shown in sensor 20 (FIG. 2), sixteen electrodes 35 are included within sensor 33 (FIG. 3). Where an even number of electrodes are arranged equiangularly about a full circle surrounding the central common electrode, diametrically opposed electrodes can be made to function in unison. However, it is also possible to obtain grain angle information through capacitive coupling across a wood specimen with the second electrode means consisting of as few as three electrodes positioned along a partial arc concentric with the sensor axis. In the general theoretical description, these ideas are developed more fully, and the alternatives just discussed will be seen to fit into a family of sensors satisfying certain constraints.

In place of a central common electrode in the first electrode means, a concentric annular electrode might serve as the common electrode. Furthermore, the sensor might be constructed in a succession of annular modules or rings each including a first common electrode and a plurality of angularly spaced second electrodes. All of these available variations will be more evident after reviewing the method of using the sensor, its theory of operation, and the general theoretical description.

Referring now to FIG. 4, the general geometry of the reference plane in sensor 20 is detailed with respect to the sensor axis A—A shown in FIG. 2.

The geometry of the radio frequency fields used to obtain grain angle information in a specimen of wood can be related to a series of first and second areas corresponding to either the operational surfaces of the first and second electrode means in the sensor 20 or to the corresponding coupled areas on the wood specimen surface adjacent to the electrodes 25, 26. For purposes of the present analysis, the central common first area is identified by the numeral 9 and the surrounding second areas spaced from it are identified by numerals 0 through 7. The center of area 9, indicated at point A, is intersected by the sensor axis A—A which is substantially perpendicular to the wood surface. A transverse horizontal half-plane with its boundary being the sensor axis and including the right half of line B—B shown in FIG. 4 defines a "zero reference" half-plane and is useful in determining the angular positions of the second areas 0 through 7, which are shown in a counterclockwise sequence about the sensor axis A—A.

The angular positions of the second areas about the sensor axis are the angles $M_0$, $M_1$, ..., and $M_7$ from the zero reference half-plane to probing half-planes, the half-planes being shown as half-lines $p_0$, $p_1$, ..., and $p_7$ in FIG. 4. These probing half-planes all begin at the sensor axis A—A and extend outward from it in a direction to intercept the corresponding second areas 0-7 on the sensor or wood surface. One can think of this "sheave" of half-planes including the reference and probing half-planes as being like the pages of a book all emanating from a common line at the spine.

While not essential to the geometry of the sensor and its functions, the areas 0 through 7 are illustrated as being equi-angularly positioned around the sensor axis A—A. This arrangement permits diametrically opposite electrodes 26 in sensor 20 to be wired to one another and to cooperatively produce or to sense fields aligned generally along parallel pairs of the probing half-planes containing the sensor axis A—A and passing through their corresponding second areas 0 through 7.

Theory of Operation

To understand the idea of using capacitor electrodes to measure grain angle, it is first necessary to understand the mathematical model of a simple two electrode geometry relative to a board 22.

Figure 6:
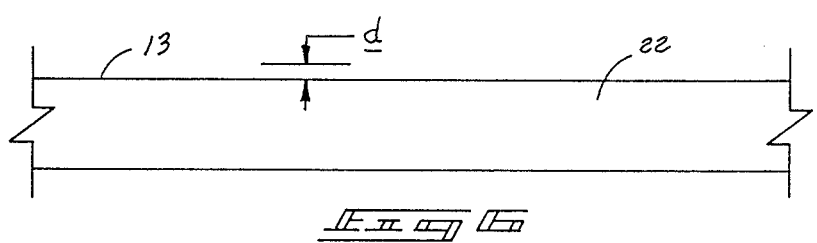
FIG. 6 is an elevation view complementary to FIG. 5.

Consider two coplanar conductive capacitor electrodes 11, 12 arranged in a plane parallel to but spaced a distance d away from a plane wood surface 13 as shown in FIG. 5 and 6.

The electrodes 11,12 have a gap g between them such that a probing plane P, perpendicular to the edges of the gap and perpendicular to the plane of the electrodes is oriented at angle M relative to a reference plane R that is also perpendicular to the plane of the electrodes. The grain angle G is the angle from the reference plane R to a wood fiber plane which is perpendicular to the plane of the electrodes and parallel to the wood fibers in the vicinity of the electrode gap. The dielectric material that influences the capacitance between the two capacitor electrodes consists of the material between and surrounding the two electrodes 11, 12. The field theory developed for two semi-infinite planes can be used to state that the largest contribution to capacitance comes from the region in and near the gap between the electrodes. Larger gaps g enlarge the region of greatest effect, and one can surmise that greater reading depths and less sensitivity to the spacing d will result, although larger gaps also reduce the capacitance. Because of the anisotropic permittivity of the wood dielectric and the dielectric combination of wood, air, and backing material for the capacitor electrodes, a complete mathematical solution of this problem would be quite complex.

The anisotropy of the wood permittivity causes the capacitance C between the two electrodes to vary sinusoidally with twice the angle M—G from the wood fiber plane to the probing plane. The capacitance is maximum when the electric field from the capacitor electrodes is applied in a direction along the wood fibers, that is when the probing plane and the wood fiber plane are aligned (M—G=0). The capacitance is minimum when the probing plane and the wood fiber plane are perpendicular to each other (M—G=90 degrees). The model we use that fits is:

$$C = C_o + C_v \cos(2(M-G)) \qquad (1)$$

The sinusoidal nature of the capacitance with respect to angle fits the experimental evidence gained from work with the mechanically rotating heads in present-day commercial grain angle measuring instruments. The term $C_o$ is an isotropic component of capacitance proportional to the isotropic component of permittivity near the gap between the electrodes, and the factor $C_v$ is the magnitude of the anisotropic component of capacitance, proportional to the anisotropic component of permittivity in direction G near the gap. Both $C_o$ and $C_v$ vary with wood density, spacing to the wood surface and moisture content. A measurement of grain angle should have as a feature an insensitivity to these confounding variables. This was achieved with the mechanically rotating head instrument because in that case the angle M in equation (1) increases at a constant rate, and equation (1) becomes:

$$C = C_o + C_v \cos(2(wt-G)) \qquad (2)$$

where w is the mechanical rotational speed in degrees/second and t is a running time variable. Equation (2) clearly shows a sinusoid of frequency twice the mechanical rotation rate where the phase has been modulated by twice the grain angle. Therefore, phase detection techniques applied to a rotating measurement of capacitance can be used to obtain the grain angle value independently of $c_o$ and $c_v$.

The measured permittivity of wood is a function of the measurement frequency as well as of grain angle and other parameters. The mechanically rotating sensor system has utilized radio frequency energy at approximately 500 KHz applied to the rotating sensor electrodes. Consequently, the signal processing requires an amplitude demodulation step to obtain the measure of capacitance shown in Equation 2. The choice of waveform and frequency range for the energy of the applied field depends on the application. A similar choice is necessary for the present invention.

"Division" Method

Four interesting special cases of equation (1) were noted for probing half-plane angles M of 0, 45, 90, and 135 degrees. For these cases:

$$C_0 = C_o + C_v \cos 2G \quad (3a)$$

$$C_{45} = C_o + C_v \cos (2G - 90) \quad (3b)$$

$$C_{90} = C_o + C_v \cos (2G - 180) \quad (3c)$$

$$C_{135} = C_o + C_v \cos (2G - 270) \quad (3d)$$

If $C_0$, $C_{45}$, $C_{90}$, and $C_{135}$ could be simultaneously measured at substantially the same location on the lumber such that $C_o$ and $C_v$ are substantially identical for all four measurements, then subtraction yields:

$$A = C_0 - C_{90} = 2C_v \cos 2G \quad (4a)$$

$$B = C_{45} - C_{135} = 2C_v \sin 2G \quad (4b)$$

which are independent of $C_o$, and a subsequent division yields:

$$B/A = \tan 2G \quad (5)$$

which is independent of $C_v$. The angle G can then be obtained from $$G = +0.5 \tan^{-1}(B/A) \quad (6)$$

Singularities in the tangent function present practical problems in solving equation (6) for angles G near ±45 degrees. Also, the tangent function has an ambiguity of 90 degrees in the resolution of angle G. Both difficulties are easily resolved by testing the numerator B and the denominator A for sign and for their relative size, and then taking advantage of known trigonometric relationships. Slightly different computations are performed depending on the results of these comparisons. The following table summarizes a set of practical rules that can be used to obtain grain angle G from A and B. some overlap of procedure is allowed; for example, the table suggests limiting the computation $G = +0.5 \tan^{-1}(B/A)$ to the situation where magnitude B is less than magnitude A, i.e. $-22.5 < G < 22.5$ degrees. However, the relationship is valid so long as $A > 0$, i.e. $-45 < G < 45$ degrees; but, for practical purposes, it is necessary to tighten the limits so that the magnitude of B/A is not too large.

| Conditions | Angle G Computation (degrees) |
|---|---|
| $A < 0$ and $B = 0$ | $+/-90$ |
| $A < 0$ and $A < B < 0$ | $-90 + 0.5\tan^{-1}(B/A)$ |
| $A < 0$ and $A = B$ | $-67.5$ |
| $B < 0$ and $B < A < -B$ | $-45 - 0.5\tan^{-1}(A/B)$ |
| $A > 0$ and $A = -B$ | $-22.5$ |
| $A > 0$ and $-A < B < A$ | $+0.5\tan^{-1}(B/A)$ |
| $A > 0$ and $A = B$ | $+22.5$ |
| $B > 0$ and $-B < A < B$ | $+45 - 0.5\tan^{-1}(A/B)$ |

| Conditions | Angle G Computation (degrees) |
|---|---|
| $A < 0$ and $-A = B$ | $+67.5$ |
| $A < 0$ and $0 < B < -A$ | $+90 + 0.5\tan^{-1}(B/A)$ |

It is likely for many purposes that only $+0.5 \tan^{-1}(B/A)$ need be computed. For example, when applied to production-line strength estimation of lumber, the accuracy of grain angle measurement has been shown to be practically unimportant for grain angle magnitudes that are large. The approach uses grain angle measurements as provided within the dynamic range allowed by tan 2G so long as cos 2G is positive. If these conditions are not satisfied, the grain angle result is treated only as "bad" and is lumped into a common category with other "bad" results. The tensile strength estimation algorithm gives equal treatment to regions of the wood having grain angle G such that either the magnitude of tan 2G is large or cos 2G is negative. These regions of the wood contribute very little (contribution can be set to zero) to the strength in the strength estimation algorithm.

It is clear that the inverse tangent computation or even the division of B by A may not be necessary to apply the method because thresholding of either the quotient B/A or identifying regions of the two-dimensional space formed with A and B as coordinates may be sufficient for the application.

We define the "division" method as any method utilizing equipment of the type described above and processing that includes dividing one signal that is essentially independent of $C_o$ by another signal that is also independent of $C_o$ to get a known function of grain angle that is essentially independent of both $C_o$ and $C_v$. One implementation of the division method utilizes two different multiple combinations of the electrodes in the second electrode means. Proper definition of the driving or sensing functions causes an effective alternate switching from one combination, Phase A, to the other, Phase B. Using time multiplexing methods, different sensed results for Phase A and Phase B can be obtained. A switching rate from Phase A to Phase B and back of about 8 KHz or faster is sufficient to effectively "freeze" the motion of production speed lumber at the highest known production-line speeds. All of the experimental results to date utilize a Phase A/Phase B cycle rate of about 8 KHz. Division of the Phase B result by the Phase A result yields the tangent of twice the grain angle. The "division" method of processing the sensed signals from this apparatus allows a particularly simple implementation and is directly suited to the problem of tensile strength estimation in lumber.

The above analysis provided the basis which led to the new sensor geometry and the most efficient means of measuring $C_0$, $C_{45}$, $C_{90}$, and $C_{135}$ for implementing equations (4), (5) and (6).

After exploring a number of configurations with this analysis format and developing an intuitive feel for the problem, the present new electrode geometry was discovered. This geometry not only allows a simple sensitive implementation for measuring the capacitances of equations (3), but it also can accomplish the arithmetic of equations (4) inherently by nature of the electrode geometry.

The geometry of the capacitor electrodes used to make the measurements of equations (3) must satisfy several requirements.

1. Measurement of all four quantities in equations (3) needs to occur almost simultaneously at substantially the same location on the wood.
2. The arrangement should allow at least some slight perturbations from parallel of the wood and the electrode operative surfaces.
3. Symmetrical electrical connection to the electrodes should be possible to minimize differences in stray circuit capacitance.
4. Some means to reduce or eliminate the problem of switching between drive and sense electrodes must be developed.
5. The approach should allow large drive voltages for increased signal-to-noise ratio.

FIG. 2 illustrates an example of the new electrode geometry which satisfies or essentially satisfies these requirements.

An important feature of this geometry is the single sense electrode 25 in the center of the array. The eight electrodes 26 surrounding the sense electrode 25 are drive electrodes. The ring 32 surrounding them is a guard ring normally tied to ground so as to define a circularly symmetric region of constant potential outside the electrode array. Diametrically opposite drive electrodes 26 are electrically connected together and are driven with a common drive signal. Small signal analysis methods can be used to show that the effects of diametrically opposite drive electrode to common sense electrode capacitances have counterbalancing effects to small perturbations from parallel between the wood and the sensor reference surfaces. Four signals drive the resulting four diametrically opposed pairs of drive electrodes 26 and one sense signal is taken from the center sense electrode 25. These are permanent connections, as this geometry does not require switching of the electrodes between sense and drive circuits. By modulating the drive signal to each pair of drive electrodes 26, and then demodulating the sense electrode signal at sense electrode 25, the arithmetic of equations (3), (4), (5) and (6) can be implemented.

Requirement 1. above insists that all four quantities in equations (3) be measured almost simultaneously. The purpose is to obtain these quantities while they have the same values of the variables $C_o$, $c_v$, and G. In a production-line machine, relative motion between lumber and grain angle detector can cause $C_o$, $C_v$, and G to change. However, if the equation (3) quantities are measured in a time interval short enough that the relative motion is sufficiently small, then the purpose is achieved. This is analogous to requiring a fast shutter speed when photographing a moving subject.

Figure 7:
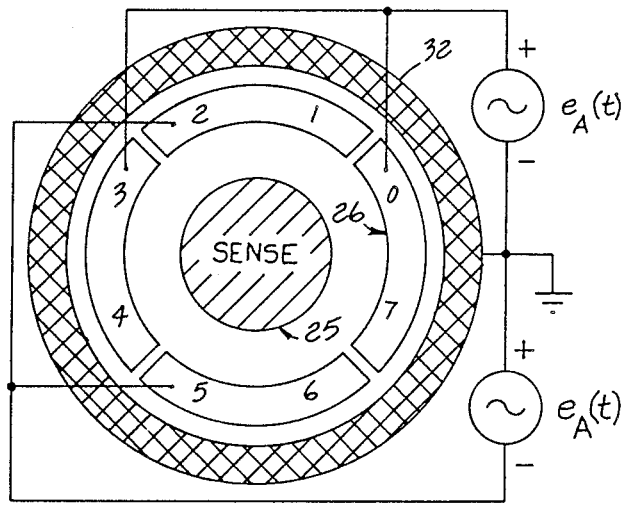
FIG. 7 is a schematic view illustrating a first phase of operation of the sensor.
Figure 8:
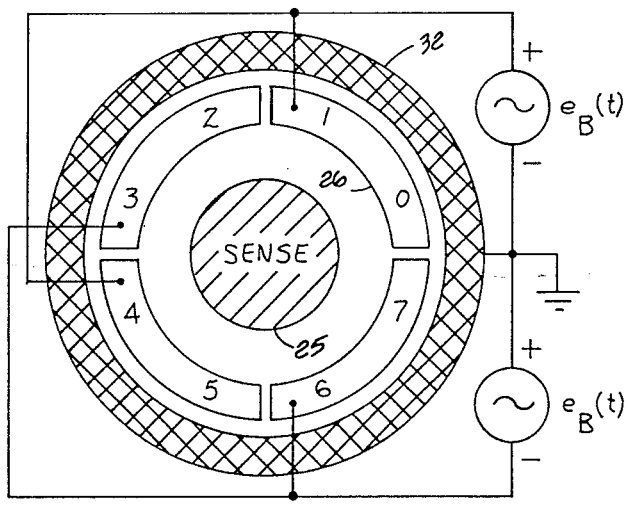
FIG. 8 is a similar schematic view illustrating a second phase of operation.

Two phases of operation describing the drive signals from an oscillator signal circuit or source are defined and illustrated in FIGS. 7 and 8. During Phase A, electrodes 1, 2, 5 and 6 are driven with the time varying potential signal $-e_A(t)$, and electrodes 3, 4, 7 and 0 are driven with the opposite polarity signal $e_A(t)$. For Phase A the effective electrode geometry is as shown in FIG. 7.

Similarly, during Phase B, electrodes 0, 1, 4 and 5 are driven with the time varying potential signal $e_B(t)$, and electrodes 2, 3, 6 and 7 are driven with the opposite polarity signal. The effective electrode geometry for Phase B is shown in FIG. 8. Phases A and B are active alternately, and the switching speed between them is adjusted so the changes in $C_o$, $C_v$, and G are negligible during each complete cycle of Phase A and Phase B.

Figure 9:
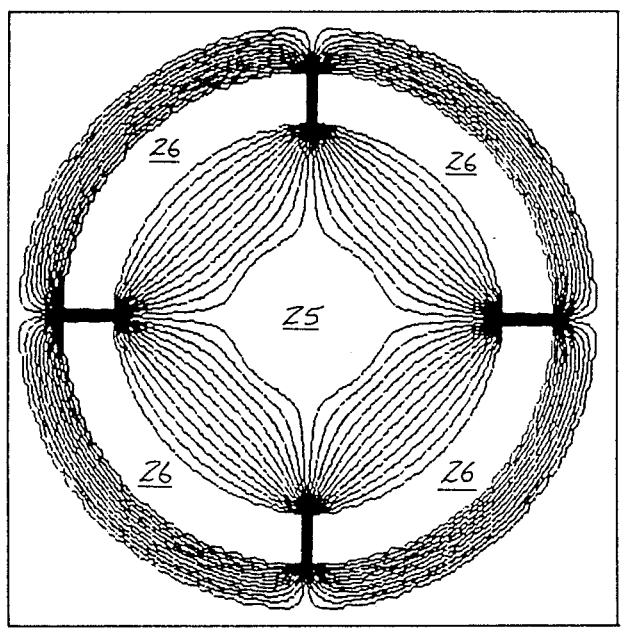
FIG. 9 is a plan view illustrating lines of equal electrical potential created by operation of the sensor.

To understand how the geometry works during Phases A or B, consider the electric field pattern during a moment of Phase B when electrodes 0, 1, 4 and s have positive potential and electrodes 2, 3, 6 and 7 have negative potential. FIG. 9 shows lines of equi-potential in the plane of the electrodes 25, 26. If we use this two-dimensional result to guide our intuition for the three-dimensional situation of interest, we can visualize equi-potential surfaces surrounding the electrodes. The electric flux lines will intercept the equi-potential surfaces at right angles. Thus, for quadrants 1 and 3 (containing drive electrodes 0, 1, 4 and 5), the electric flux lines probe the wood dielectric in planes essentially perpendicular to and intersecting the electrode array at angle 45 degrees. This is the same probing direction as for the capacitor electrodes of FIG. 5 with M=45 degrees. Consequently, a measure of capacitance from drive electrodes 0, 1, 4, and 5 in quadrants 1 and 3 to the sense electrode 25 is similar to a measure of capacitance $C_{45}$ of equation (3c). Likewise, a measure of capacitance from the drive electrodes 2, 3, 6, and 7 in quadrants 2 and 4 to the sense electrode 25 is similar to a measure of capacitance $C_{135}$ of equation (3d).

Figure 10:
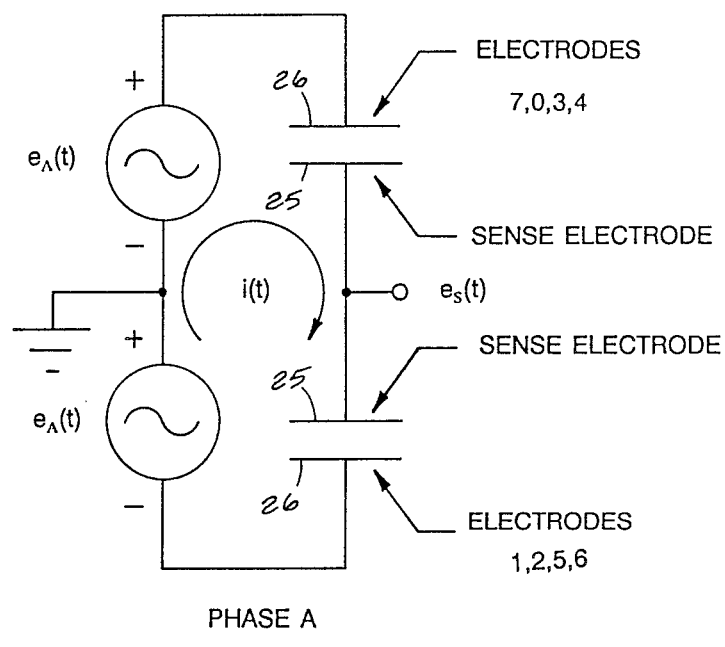
FIG. 10 is a schematic circuit diagram showing the first phase of operation.
Figure 11:
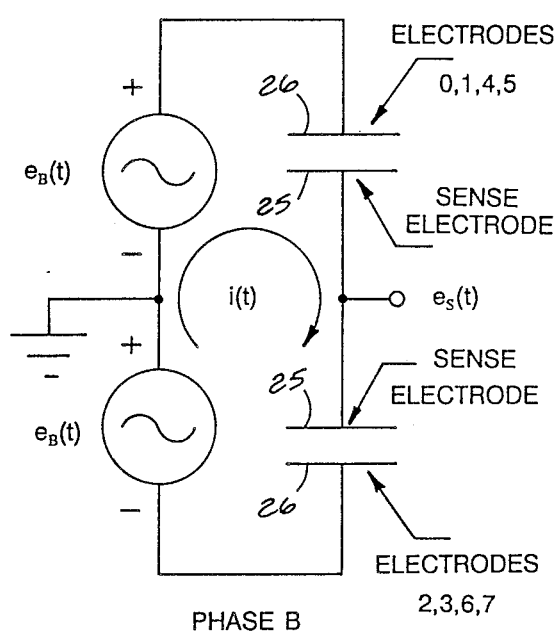
FIG. 11 is a similar schematic circuit diagram showing the second phase of sensor operation.

The sense electrode 25 is a conductor and therefore everywhere at the same potential; however, in determining just what that potential is, the electrical models of FIGS. 10 and 11 are helpful.

From FIG. 11, assuming zero initial conditions (not a problem because in this case, initial charges on the capacitors lead to a dc component which is not seen by the detection process) one can write the loop voltage equations:

$$2e_B(t) - (1/C_{45})\int_0^t i(u)du - (1/C_{135})\int_0^t i(u)du = 0$$

$$e_S(t) = e_B(t) - (1/C_{45})\int_0^t i(u)du$$

Solving these equations for $e_S(t)$ after first substituting from equations (3b) and (3d) yields:

$$e_S(t) = (C_v/C_o)(\sin 2G)e_B(t) \tag{7a}$$

The output $e_S(t)$ during Phase B is an amplitude modulated version of $e_B(t)$. Demodulation yields:

$$B = (C_v/C_o)\sin 2G \tag{8a}$$

In the same way, for Phase A drive signals, the field probing pattern from the drive electrodes to the sense electrode can be shown to measure capacitances similar to $C_0$ and $C_{90}$ of equations (3a) and (3b). In that case the output $e_S(t)$ becomes:

$$e_S(t) = (C_v/C_o)(\cos 2G)e_A(t) \tag{7b}$$

Demodulation yields:

$$A = (C_v/C_o)\cos 2G \tag{8b}$$

A division of (8a) by (8b) results in:

$$B/A = \tan 2G \tag{9}$$

It is to be noted that the subtraction of equations (4) has been effectively accomplished by the electrode geometry to yield equations (8a) and (8b) and further that A and B in equations (8a) and (8b) are normalized by $C_o$. This makes A and B inherently less sensitive to density variations, electrode array-to-wood spacing, and moisture content variations because these changes can be expected to cause the values $C_o$ and $C_v$ to change generally in the same direction. The ratio $C_v/C_o$ is more stable with density, spacing and moisture content than either $C_o$ or $C_v$ would be independently. Consequently, the dynamic range requirements for the circuitry are reduced from those that could be inferred from equations (4). This inherent normalization effect is a significant unanticipated advantage of the new sensor geometry.

Drive Signals

Figure 12:
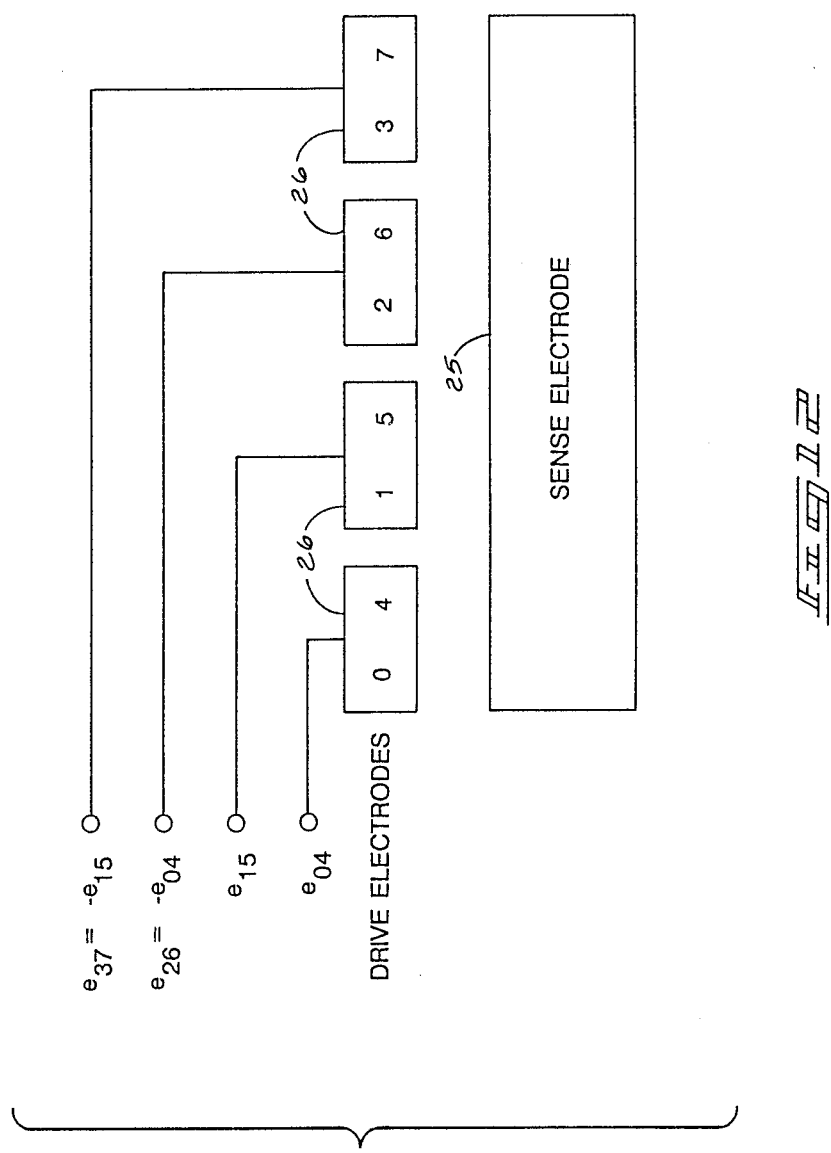
FIG. 12 is a diagrammatic view illustrating the wiring connection to the drive electrodes in the sensor.

FIG. 10 shows drive signals $e_A(t)$ connected to electrodes 7, 0, 3, and 4, and $-e_A(t)$ connected to electrodes 1, 2, 5, and 6 during Phase A. During Phase B (FIG. 11), the connections are $e_B(t)$ to electrodes 0, 1, 4, and 5 and $-e_B(t)$ to electrodes 2, 3, 6, and 7. FIGS. 10 and 11 are convenient for analyzing the performance of the electrode geometry, but obscure the fact that there is no need to switch signals to the electrodes from Phases A to B as the figure seems to indicate. Instead, consider FIG. 12. FIG. 12 shows that electrodes 2 and 6 are driven with the negative of the signal $e_{04}$ applied to electrodes 0 and 4; and similarly electrodes 3 and 7 are driven with the negative of the signal $e_{15}$. This is consistent with FIGS. 7 and 8 and FIGS. 10 and 11 for both Phases A and B. Further, one can set $e_{15} = -e_{04}$ during Phase A, and set $e_{15} = +e_{04}$ during Phase B.

In equation (7a), the signal $e_B(t)$ is:

$$e_B(t) = e_{04}(t) = e_{15}(t), \text{ during Phase B}$$

and, in equation (7b), the signal $e_A(t)$ is:

$$e_A(t) = e_{04}(t) = -e_{15}(t), \text{ during Phase A.}$$

The Carrier Signal

One can choose a carrier signal $e_c(t)$ and from it define the electrode drive signals according to the previous section:

$$e_{04}(t) = e_c(t)$$

$$e_{15}(t) = \begin{cases} -e_c(t), \text{ during Phase A} \\ +e_c(t), \text{ during Phase B} \end{cases}$$

$$e_{26}(t) = -e_c(t)$$

$$e_{37}(t) = \begin{cases} +e_c(t), \text{ during Phase A} \\ -e_c(t), \text{ during Phase B} \end{cases}$$

Rewriting equations (7) yields:

$$e_s(t) = (C_v/C_o)(\cos 2G)e_c(t), \text{ during Phase A} \quad (10a)$$

$$e_s(t) = (C_v/C_o)(\sin 2G)e_c(t), \text{ during Phase B} \quad (10b)$$

This result shows clearly the amplitude modulation $(C_v/C_o)\cos 2G$ during Phase A and $(C_v/C_o)\sin 2G$ during Phase B.

The sense voltages given by equations (10a) and (10b) do not occur simultaneously. Thus, division of equation (10b) by (10a) at a common time of occurrence to yield $\tan 2G$ does not occur in this implementation. However, if the modulation signals $(C_v/C_o)\sin 2G$ and $(C_v/C_o)\cos 2G$ have negligible variation over one cycle of Phase A and Phase B, they can be stripped from the carrier $e_c(t)$ by a demodulation process, the demodulated signals stored (or sampled and held), and the division accomplished.

So far, the carrier $e_c(t)$ has not been specified. Successful capacitive probing of wood for grain angle in the past has used sinusoidal signals of approximately 500 KHz. The dielectric permittivity of wood is a function of frequency, but not a strong function of frequency in the frequency range from 500 KHz to 50 MHz. Consequently it should be expected that a broad range of carrier waveforms having frequency components between 500 KHz and 50 MHz would be satisfactory. In particular, either a sine wave or a square wave at 500 KHz will work.

Amplitude Demodulation

A signal $f_m(t)$ that amplitude modulates a periodic carrier $e_c(t)$ can be obtained by a synchronous demodulation process if the carrier signal is available, which it is in this case. The modulated carrier is:

$$f(t) = f_m(t)e_c(t)$$

Synchronous demodulation can occur by multiplying $f(t)$ by $e_c(t)$ and then integrating over a period. Explicitly, the result of these operations is:

$$\begin{aligned} g(t) &= (1/T) \int_{t-T}^{t} f_m(u) e_c^2(u) du \\ &= (1/T) f_m(t) \int_{t-T}^{t} e_c^2(u) du \end{aligned}$$

where the approximation of pulling $f_m(t)$ out of the integral is good provided that the change in $f_m(t)$ is small over the interval $(t-T, t)$. If $e_c(t)$ is periodic with period T, then the integral is a constant and:

$$f_m(t) = Qg(t)$$

where Q is a constant.

Alternatively, even if $e_c(t)$ is not periodic, synchronous demodulation can occur by multiplying by $e_c(t)$ and then passing the result through a low-pass filter. With a simple, single pole filter having time constant z, this can be shown equivalent to integrating with an exponential weighting function so that the result of these operations is:

$$g(t) = (1/z) \int_{-\infty}^{t} f_m(u)e_c^2(u)\exp(-(t-u)/z)du$$

2

The most recent components of $f_m(t)e_c(t)$ are weighted most heavily in the integral. If $f_m(t)$ has negligible change over time intervals of approximately $10z$ or more, and if the energy of $e_c(t)$ in all equal length intervals is essentially the same for intervals of length greater than about 10z, then the integral can be simplified, as before:

$$f_m(t) = Qg(t)$$

where Q is essentially a constant.

"Rotation" Methods

We have investigated several methods of modulating the drive signals applied to the electrodes of FIG. 2. In these cases diametrically opposite electrodes are connected together, and at any instant the applied potentials on drive electrodes at orthogonal positions around the array are equal in magnitude but opposite in sign. With these basic features of drive signal definition, there are several methods of driving the second electrodes and processing the signal sensed at the common first electrode, other than the "division" method described, that yield accurate grain angle measurements. This group of methods shall be termed "rotation" methods.

FIELD PATTERN ROTATES AT ONE-HALF CARRIER FREQUENCY RATE

Let the drive on the drive electrodes be:

| Electrodes | Drive Voltage |
|---|---|
| 0,4 | $e_{04}(t) = e_c(t)$ |
| 1,5 | $e_{15}(t) = e_c(t - T/4)$ |
| 2,6 | $e_{26}(t) = e_c(t - T/2)$ |
| 3,7 | $e_{37}(t) = e_c(t - 3T/4)$ (11) | where $e_c(t)$ is periodic with period T and satisfies $$e_c(t - T/2) = -e_c(t)$$

This last condition is imposed to ensure that orthogonally aligned electrodes have applied potentials that are equal in magnitude but opposite in sign.

With these drive signals, the sense electrode potential $e_s(t)$ can be obtained by superposition of results from electrodes 0, 4, 2 and 6 and from electrodes 1, 5, 3 and 7 to give:

$$e_s(t) = (C_v/C_o)(\cos(2G-45))e_c(t)$$

$$+ (C_v/C_o)(\sin(2G-45))e_c(t-T/4) \quad (12)$$

Smooth Rotation (Sinusoidal Carrier)

Let:

$$e_c(t) = \cos(w_c t - 45)$$

where $w_c/360$ is the frequency of the carrier in Hz. Then:

$$\begin{aligned}e_s(t) &= (C_v/C_o)(\cos(2G - 45)\cos(w_c t - 45) + \\ &\quad \sin(2G - 45)\sin(w_c t - 45)) \\ &= (C_v/C_o)\cos(w_c t - 2G)\end{aligned} \quad (13)$$

This result is a phase modulated carrier with the phase modulation being $-2G$. standard phase demodulation methods may be used to demodulate this signal and obtain the phase $-2G$ and hence the grain angle G.

Discrete Rotation (Square Wave carrier)

Figure 13:
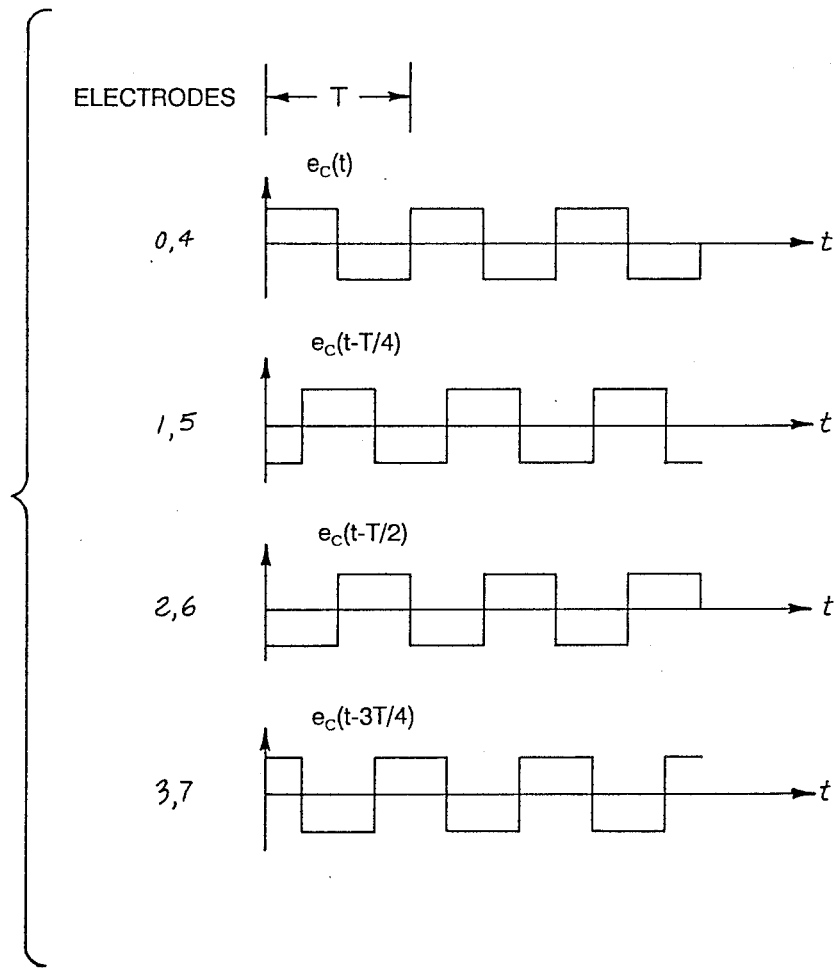
FIG. 13 is a timing diagram illustrating one method of operating the sensor.
Figure 11:
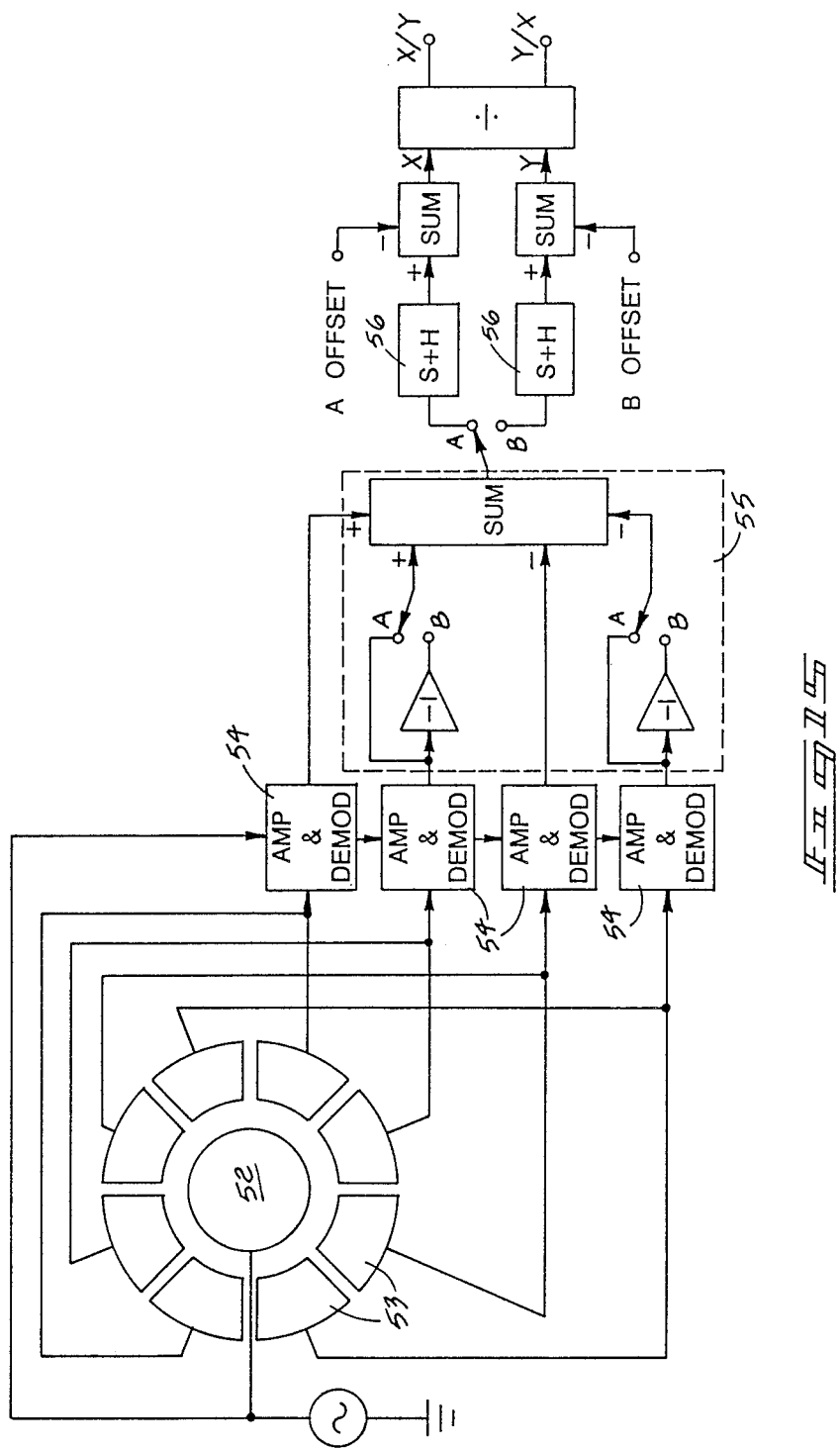

Let $e_c(t)$ be a square wave at frequency $w_c/360$ Hz such that $$e_c(t) = \begin{cases} +1, & nT \leq t < T/2 + nT \\ -1, & T/2 + nT \leq t < (n+1)T \end{cases} \quad (14)$$

where n is an integer and $T = 360/w_c$ seconds is the period. Then from equation (11) the drive signals to the electrodes appear as in FIG. 13.

For $0 \leq t < T/4$, electrodes 0, 4, 3 and 7 are positive, and electrodes 1, 5, 2 and 6 are negative. Similarly, for the other 3 quarters of the period T, the electrode polarities are determined. The result is:

| Time Interval | Positive Electrodes | Negative Electrodes |
|---|---|---|
| $0 \leq t < T/4$ | 0, 4, 3, 7 | 1, 5, 2, 6 |
| $T/4 \leq t < T/2$ | 0, 4, 1, 5 | 2, 6, 3, 7 |
| $T/2 \leq t < 3T/4$ | 1, 5, 2, 6 | 0, 4, 3, 7 |
| $3T/4 \leq t < T$ | 2, 6, 3, 7 | 0, 4, 1, 5 (15) |

By substituting the definition of $e_c(t)$ from equation (14) into equation (12), we deduce that except for a scale factor, the sense electrode signal is:

| Time Interval | Sense Electrode Signal, $e_s(t)$ |
|---|---|
| $0 \leq t < T/4$ | $(C_v/C_o)\cos 2G = C_v/C_o \cos(w_c t - 2G)\|t=0$ |
| $T/4 \leq t < T/2$ | $(C_v/C_o)\sin 2G = C_v/C_o \cos(w_c t - 2G)\|t=T/4$ |
| $T/2 \leq t < 3T/4$ | $-(C_v/C_o)\cos 2G = C_v/C_o \cos(w_c t - 2G)\|t=T/2$ |
| $3T/4 \leq t < T$ | $-(C_v/C_o)\sin 2G = C_v/C_o \cos(w_c t - 2G)\|t=3T/4$ (16) |

Here, $e_s(t)$ is seen to be the sampled version of equation (13) where sampling occurs at the four sample times $t=0, T/4, T/2$, and $3T/4$ for each period. Use of a low pass filter can in principle result in recovery of the waveform $\cos(w_c t - 2G)$ from which phase demodulation can be used to obtain the grain angle G. In practice, it would be better to sample the waveform at more than four points per period of equation (13). There is nothing to prevent increasing the number of electrodes and reducing the 45 degree geometric step size of the discrete rotation implied by equation (15). The number of electrodes must be divisible by 4 and most conveniently should be a power of 2. Filtering requirements to recover the waveform $\cos(w_c t - 2G)$ from the sampled and held version are less stringent when more samples per period are available. From equation (16), it is clear that the sine and cosine results also could be used directly in the "division" method if desired.

FIELD PATTERN OSCILLATES AT THE CARRIER FREQUENCY RATE AND ROTATES AT ONE-HALF A LOWER SUBCARRIER FREQUENCY RATE

The advantage here is that the field rotation rate is uncoupled from the signal best suited for probing the dielectric properties of wood. The subcarrier frequency must be high enough to ensure negligible variation in $C_v$ and $C_o$ over one period and to allow adequate time resolution in measuring a changing grain angle G.

Let the drive on the drive electrodes be:

| Electrodes | Drive Voltage |
|---|---|
| 0,4 | $e_{04}(t) = e_m(t)e_c(t)$ |
| 1,5 | $e_{15}(t) = e_m(t-T_m/4)e_c(t)$ |
| 2,6 | $e_{26}(t) = e_m(t-T_m/2)e_c(t)$ |
| 3,7 | $e_{37}(t) = e_m(t-3T_m/4)e_c(t)$ (17) | where $e_m(t)$ is periodic with period $T_m$ such that $$e_m(t-T_m/2) = -e_m(t)$$

By superposition of results from electrodes 0, 4, 2 and 6 and from electrodes 1, 5, 3 and 7, the sense electrode voltage is:

$$e_s(t) = (C_v/C_o)((\cos(2G-45))e_m(t) + (\sin(2G-45))e_m(t-T_m/4))e_c(t) \quad (18)$$

Note that the carrier $e_c(t)$ can be any signal which we can remove by amplitude demodulation from $e_s(t)$ in equation (18) to obtain the modulation component.

Smooth Rotation (Sinusoidal Subcarrier)

Let:
$$e_m(t) = \cos(w_m t - 45)$$

where $w_m/360$ is the frequency of the subcarrier in Hz. Then:

$$\begin{aligned} e_s(t) &= (C_v/C_o)(\cos(2G-45)\cos(w_m t - 45) + \\ &\quad \sin(2G-45)\cos(w_m(t-T_m/4)-45))e_c(t) \\ &= (C_v/C_o)\cos(w_m t - 2G)\, e_c(t) \end{aligned} \quad (19)$$

where $T_m = 360/w_m$ seconds is the period of the subcarrier. The carrier can be stripped off, and phase demodulation methods can be used as before. The signal processing methods for extracting the angle G from the result in equation (19) can be identical to the methods used with the successful mechanically rotating head implementation of grain angle measurement. The difference is in the means of generating the subcarrier frequency $w_m$. In the mechanical rotating version, the rotation itself produces a subcarrier frequency equal to twice the mechanical rotation rate. In the present case, two phases (sine and cosine) of the subcarrier are generated electronically and are used to modulate the carrier $e_c(t)$. The advantage of the electronically produced subcarrier method is the absence of moving parts and a much greater range of feasible subcarrier frequencies.

Discrete Rotation (Square Wave Subcarrier)

Let:

$$e_m(t) = \begin{cases} +1, & nT_m \leq t < (n+1/2)T_m \\ -1, & (n+1/2)T_m \leq t < (n+1)T_m \end{cases} \quad (20)$$

where n is an integer. The analysis is similar to that for the case of discrete carrier rotation. An intermediate demodulation processing step removes the carrier. The result is a sampled, amplitude-demodulated version of equation (19) which can be filtered and phase detected for G. Increasing the number of capacitor electrodes increases the number of samples per period just as for the case of discrete carrier rotation.

Circuit Implementations

FIG. 14 schematically illustrates an example of the circuitry that can be used in conjunction with sensor 20 to carry out the above-described "division" method of processing sensor signals to produce a quantified value that is a function of grain angle.

The drive signals for electrodes 26 are derived from an oscillator 40. The signal produced by oscillator 40 is frequency divided to get a carrier signal EC switching between logic zero and logic one at frequency 500 KHz. This is further frequency divided to get a logic control signal AB at frequency 7.8125 KHz. The logic signals EC and AB are inputs to an EXCLUSIVE OR circuit 41 whose output ECM can be viewed as the carrier EC amplitude modulated with the control signal AB. The signals EC and its complement EC are inputs to a differential input, differential output amplifier 42. The amplifier 42 outputs drive a transformer 43 which scales up the logic level signal voltages to obtain the electrode drive signal E04 and its negative E26. Satisfactory operation has been observed with peak-to-peak voltages of about 60 volts. Greater voltage yields greater sensitivity. Similarly the signals ECM and its complement ECM are used to obtain the plate drive signal E15 and its negative E37.

The potential at the sense electrode 25 is detected through a short length of shielded cable 44 by a field effect transistor input amplifier 45. The amplifier 45 presents a high impedance to the sense electrode 25 to prevent distortion of the measured sense electrode potential. Low impedance at the amplifier output reduces noise contribution to the amplified signal. The signal is passed through a synchronous demodulator circuit 46 which is controlled by the 500 KHz carrier signal EC. A low-pass filter 47 completes the removal of signal components at the carrier frequency or higher.

Two sample and hold circuits 48, 49 sample the signal at the proper times to extract Phase A and Phase B information; sampling times are controlled by the signal AB and its complement. From this point the signal processing can be either analog or digital, with the Phase A and Phase B information being digitized if digital processing is used. For illustrative purposes an analog block diagram is shown. Learned offsets, stored previously as A and B outputs 50, 51 when no wood is present, are subtracted from the A and B signals. This is a method useful for removing sensor asymmetry or contamination effects and enhances the sensor's accuracy. Then, the quotient B/A is formed, followed by an inverse tangent transfer characteristic and scaling by one-half. Ambiguity of grain angles near zero and ±90 degrees is handled by testing the denominator A for sign. If A is negative the angle is known to be outside the domain ±45 degrees. Because the quotient B/A is large for grain angles near ±45 degrees, this quotient is not useful near those angles; however, then the reciprocal quotient A/B can be used. In that case, the problem of large quotient occurs for grain angles near 0 and ±90 degrees. If measurements over the whole domain of grain angles is required, then both quotients B/A and A/B should be implemented with sensing to indicate when each is to be used. For example, the sensing could simply choose the output having smallest magnitude, and ambiguities would be resolved by testing the signs of A and B.

With identical sensor geometries, dual processing methods can be used wherein the roles of the previously-described sense and drive electrodes are interchanged. In the dual configurations, instead of sensing with a single amplifier and driving multiple drive electrodes with multiple but related signals, the drive is with a single drive signal and sensing is with multiple amplifiers. By properly combining the amplifier output signals, the grain angle can be obtained.

For example, one realization of the "division" method including the Phase A / Phase B cycling could be as shown in FIG. 15. In FIG. 15 one drive signal, which can be a sinusoid, square wave, or other time varying potential signal as discussed previously is applied to a centrally located drive electrode 52 in an electrode array. Eight peripherally located sense electrodes 53 connected in diametrically opposite pairs are input to four amplifiers 54. One method of reducing the effects of stray circuit capacitances with such a method is to use charge amplifiers which can have a low input impedance that is capacitive in nature; then, the circuit strays have a smaller effect. Amplitude demodulated amplifier outputs are summed by circuits 55 as shown with signs on alternate pairs switched during the phase A and Phase B intervals. Demodulation can occur equally well either before or after summing. Sample and hold circuits 56 with sampling occurring respectively at times during Phase A and Phase B yield signals which can be processed as before to give grain angle.

Alternatively, FIG. 16 illustrates another realization of the "division" method wherein the Phase A/Phase B concept is replaced with permanent connections of the alternate pairs of peripheral sense electrodes 53 to two differential input amplifiers 57 as shown. Following amplitude demodulation, processing occurs as though the demodulated signals were the Phase A and Phase B signals.

FIG. 17 illustrates a realization utilizing phase demodulation. Through the amplitude demodulation step, FIG. 17 can be implemented identically to FIG. 16. Then the amplitude demodulated outputs at 58 are used to amplitude modulate the cosine and sine of a scanning frequency. Phase demodulation of the summed result yields twice the grain angle.

Tests and Evaluation

Several practical parameters have been identified that could affect the quality of production-line grain angle measurements of lumber. These include lumber speed, the distance and lack of parallel relationships between the sensor and wood surfaces, temperature and humidity variations, mechanical shock and vibration forces, surface contamination on the sensor and lumber, sensor size, wood moisture content, and wood surface finish. Prior experiments with existing mechanically rotating grain angle sensors have demonstrated that radio frequency techniques work well with lumber having surface characteristics, finish and moisture content typical of that produced by production sawmills.

Because the present sensor uses field strength and frequencies very similar to those used with the mechanically rotating sensors, the effect of these lumber parameters on resulting quantified values or measurements will be similar. Temperature, humidity, shock and vibration are parameters that are customarily encountered and successfully overcome in the design of electronic testing equipment for operation in a sawmill environment. There is nothing unusual about the present sensor requirements or electronic components that will require special attention to these issues. Consequently, initial testing of the sensor was restricted to investigation of five parameters: lumber speed, spacing distance between sensor and wood surfaces, wedge angle (lack of parallel relationship between the sensor and wood surface), sensor surface contamination, and sensor size. Grain angle measurements were made under test conditions and the error from a standard reference was studied for different values of each parameter set. The standard parameter set was defined as: speed=0, spacing=0.100 inch (2.54 mm), wedge angle=0 degrees, surface contamination=0, and sensor size=1 inch (2.54 cm) diameter. Investigation of the effect of the parameters was made by deviating them, typically one at a time, and comparing the measured grain angles with the standard reference.

All of the experimental results to date have utilized the "division" method of grain angle measurement. It was chosen for test purposes because it is conceptually straightforward and avoids much of the circuit complexity of alternate methods. It is also well suited for production line strength estimation which will require multiple channels of grain angle measurements. The required division was accomplished digitally, as was the subtraction of offsets from the numerator and denominator components being divided. Our experiments showed small signal components in the absence of a wood specimen, presumably due to inexactness of symmetry in the sensor electrode arrays. Large signals in the absence of a wood specimen were identified when the sensor surface was contaminated with pitch. These "offset signals" were stored and subtracted digitally from the numerator and denominator used in the division method to improve the grain angle measurement accuracy over a wider range of parameters.

The measurement of grain angle at simulated high production speeds was achieved by rotating test blocks of wood and measuring the grain angle at a location offset from the axis of rotation. In this manner, production lumber speeds could be simulated. Measured grain angles were processed for simulated lumber speeds of 89, 1216 and 1951 feet per minute (27, 371, and 595 m/min). The resulting data revealed no evidence of speed degradation.

The key to the speed capability of this system is its ability to track changes in grain angle. The sensor size or diameter provides a basic limitation in resolving spacial change in grain angle. Tests using a 1.0 inch (2.54 cm) diameter sensor illustrated responsiveness to grain angle changes without degradation over the tested speeds and proved the high speed response capability of the system. With this sensor size, useful resolution to as fine as 0.13 inch (3.3 mm) has been observed. These tests have confirmed that the grain angle sensor is effective at speeds exceeding the fastest MSR production speeds of about 1400 ft/min (427 m/min).

In production line usage, some variations of distance between the face of the sensor and the adjacent wood surface will occur as lumber moves by the sensor. Tests have been conducted for distances of 0.050, 0.100, and 0.250 inches (1.27, 2.54, and 6.35 mm). Although the discrepancy is largest at the 0.250 inch (6.35 mm) distance, the grain angle measurements have still proven useful at such a spacing. Larger sensors have sensitivity to even greater distances.

The sensor reference surface and measured wood surface may not always be parallel in production operations. To check the effect of this on measured grain angle, the sensor was tested with wedge angles between the sensor and wood surface of −2.5 and +2.5 degrees. The observed differences in relation to readings taken with parallel positions of the sensor and wood surface show the desirability of maintaining them reasonably parallel; however, at these angles the results were still useful.

The grain angle sensor measures dielectric properties of wood. If other dielectric materials are introduced in the space between the sensor and wood, they will affect the measurement. One of the more severe contamination conditions that can be expected in a production environment is sensor contamination due to contact with pitch on the lumber surfaces. To simulate this condition, pitch was heated and smeared over the sensor's operational face. The difference between measured grain angle with pitch for two different conditions were observed to be severe.

A solution to this variance is to either periodically clean the sensor face or to electronically "learn" the offsets in the processing computations that are caused by contamination. Offsets can be detected in both the numerator and denominator components of the division computation. The numerator and denominator can be corrected by subtracting the contaminant offsets before the division is carried out (see the description of FIG. 14). To test the feasibility of this correction, it was implemented with the "division" method in processing software utilized with the sensor. Offsets were learned with the test block backed away from the sensor, and these offsets were subtracted from the pitch-distorted signals with sensor to wood spacings of 0.100 inch (2.54 mm). Division of the corrected numerator by the corrected denominator was then carried out in the computer. The results demonstrated that such offset correction is an effective means of compensating for pitch contamination.

The capacitor electrode array size control the extent of the electric field produced by the sensor. Thus, the spatial resolution of the measured grain angle and the space between the wood surface and the sensor that can be tolerated are dependent on the size of the sensor. The electric field fringes into the wood primarily in the gap region between the operative surfaces of the common first electrode means and the electrodes of the second electrode means. The effective sensor area is the circle defined by the inner diameter of the surrounding electrodes in the second electrode means. Tests of the difference sizes of sensors of the type shown in FIG. 2 and previously described indicate that the decrease of signal strength away from the near the field region is exponential and further that the exponent is dependent on sensor size. Smaller diameter sensors yield results having higher resolution, but spatial resolution and distance to the wood that can still give accurate measurements are parameters that must be balanced in scaling this technology.

Technical feasibility of high speed grain angle measurements by the present apparatus and method has been proven by the tests conducted to date. These tests have verified that critical parameter variations that can be expected in a production environment can be accommodated to assure that grain angle measurement by the methods and apparatus described herein are feasible.

PROCESSING METHODS

The method for determining grain angle or other quantified values that are a function of grain angle (such as lumber grades, arbitrary sorter instruction, etc.) involves the following general steps:

(1) Applying time-varying electrical potentials to a wood specimen through a selected wood surface at one or the other of a common first area centered at a test point on the wood surface or a plurality of three or more second areas arranged about the test point on the wood surface, the potentials being applied so as to direct an electric field along probing half-planes. The probing half-planes are each bounded by a common line of intersection (called the test axis) substantially perpendicular to the wood surface at the test point and intersecting the wood surface at both the common first area and one of the second areas. A reference half-plane also bounded by the test axis is used to identify the angular position of the probing half-planes about the test axis and hence the angular position of the second areas about the test point. It will be seen from the earlier description of the sensor 20 with the sensor reference surface and the selected wood surface placed adjacent to one another with the sensor axis A—A coinciding with the wood test axis, that there is a one-to-one correspondence between the operative surfaces of the sensor's common first electrode 25 and the second electrodes 26 and the common first area and second areas of the wood surface. This correspondence includes also the probing half-planes and the reference half-plane except for opposite angle senses measured from the reference half-plane due to the mirror nature of the adjacent surfaces. It is understood that the angle sense is measured positive clockwise from the reference half-plane about the test axis looking from the sensor toward the wood surface.

(2) Sensing signals at the other of the common first area or the plurality of second areas. The sensed signals are amplitude modulated as a function of wood grain angle and the amount of anisotropy in the wood specimen in the vicinity of the test point. In the case where time-varying electrical potential is applied to the common first area, the signal sensed at each second area is a measure of permittivity in the vicinity of the test point along the corresponding probing half-plane. In the case where time-varying electrical potentials are applied to the second areas, the signal sensed at the common first area is inherently a combination of signals each of which is a measure of permittivity in the vicinity of the test point along one of the probing half-planes. The operative vicinity that is tested is the portion of the wood specimen underlying the sensor.

(3) Processing the signals to obtain the grain angle or a desired function of grain angle in the vicinity of the test point. The processing steps to produce a quantitative value from the sensed signals can take many forms, including the "division" or "rotation" methods described previously. The resulting quantitative value can be a direct measurement of grain angle or can be other quantitative values that are a function of wood grain angle such as arbitrary grading codes, automatic lumber sorter instructions to segregate boards as a result of such tests, etc.

The following section entitled "General Theoretical Description" fully discloses the conditions on the geometry, time-varying electrical potentials, and processing details which lead to favorable results. These conditions apply to the tested apparatus and specific results described earlier.

In some instances, the processing step of the method includes subtraction of sensed output signals achieved along a first probing half plane in the test specimen from those achieved along a second probing half plane to obtain a difference signal. As previously described, such subtraction is automatically achieved under certain geometric relationships between the common first and the second electrodes.

In many implementations it will be desirable to separate, in frequency, the probing signals from the scanning signals. The probing signals are chosen in a frequency band appropriate for detecting the anisotropy of permittivity in wood (our experiments have proved that 500 KHz is acceptable). The scanning signal frequency range is chosen to be high enough for the desired geometric resolution on the wood in the presence of highest expected relative speeds between wood and sensor (for our purposes 8 KHz has been sufficient). The approach is specifically not limited to sinusoids, although they can be used. Our experiments were built around logic circuitry which was particularly convenient and which gave excellent results using square waves. Application of time-varying potentials with dc offsets is acceptable.

An amplitude demodulation step to remove the probing signal will be useful in most implementations to reduce the bandwidth requirements of the processing circuitry, although there may be a choice about where in the circuitry to perform this step. For example, efficient combining steps may be possible at high frequency, and performing demodulation on the combined results may reduce the number of demodulators required. In the "General Theoretical Description" which follows, the signals are treated as though they have already had the probing signal removed.

GENERAL THEORETICAL DESCRIPTION

Given:

(1) A common first area is centered at a test point on a selected surface of a wood specimen with a test axis substantially perpendicular to the wood surface at the test point and a plurality of n (n being three or more) second areas on the wood surface arranged about the test point. Associated with the $i^{th}$ second area ($i=0, 1, \ldots, n-1$) is a probing half-plane whose boundary is the test axis and which intersects the wood surface at the common first area and the second area at its center, the half-plane being at angle $M_i$ measured clockwise from a reference half-plane. The reference half-plane has the test axis as its boundary and is aligned in a preferred manner, usually so as to intersect the wood surface in a line that is parallel with a longitudinal wood axis, as for example, along the length of a piece of lumber. Without loss of generality, assume that the wood fiber plane at the test point, defined as the plane containing the test axis and parallel to the wood fibers in the vicinity of the test point, is aligned at angle G with respect to the reference direction, where G has magnitude less than or equal to 90 degrees.

(2) A sensor with first and second electrode means, having operative surfaces corresponding to the first and second areas on the selected wood surface and located adjacent and in close proximity to the wood surface, is used to provide an electrical interface to the wood for the application of time-varying electrical potentials through the wood surface to the wood specimen and the sensing of signals from it for the purpose of measuring the grain angle G or a known function of it.

Let the capacitance between the $i^{th}$ second electrode and the common first electrode be given by $C_i$ which is proportional to the permittivity as measured by the time-varying electric field caused along the $i^{th}$ probing half-plane by the probing signal(s) applied to the electrode(s). The capacitance $c_i$ has an isotropic component and an anisotropic component corresponding to the isotropic and anisotropic components of permittivity along the $i^{th}$ half-plane. Specifically, we write:

$$C_i = C_{oi} + C_{vi} \cos(2M_i - 2G), \quad i=0, 1, \ldots, n-1 \tag{21}$$

where $C_{oi}$ is the isotropic component of capacitance between the common first electrode and the $i^{th}$ second electrode and $C_{vi}$ is the magnitude of a sinusoidal anisotropic component, the phase of the sinusoid being determined by angles G and $M_i$.

By driving either the first or the second electrode means with time-varying potential(s), sensing the resulting signal(s) at the other electrode means, and demodulating to remove the probing frequencies according to methods described earlier, derived signals $S_i$ proportional to the capacitances $C_i$ in equation (21) can be obtained. Without loss of generality let $$S_i = C_i \tag{22}$$

Define m composite signals $V_j(S_0, S_1, \ldots, S_{n-1})$, $j=0, 1, \ldots, m-1$ as functions of the signals $S_i$ and restrict attention to the special case of this where the functions are weighted sums of the signals (linear combination). Splitting the weighted sums into isotropic and anisotropic components yields:

$$V_j = \sum_{i=0}^{n-1} u_{ji} S_i \qquad (23)$$
$$= \sum_{i=0}^{n-1} u_{ji} C_{oi} + \sum_{i=0}^{n-1} u_{ji} C_{vi} \cos(2M_i - 2G)$$

where $u_{ji}$ is the weight used with the $i^{th}$ signal $S_i$ for the $j^{th}$ combination. This form reveals a useful restriction that can be imposed; namely, that the first sum be zero. This is intuitively useful because in the absence of any anisotropic dielectric material, for example if we remove the wood, it is desirable to have zero signal. Thus:

Restriction (i) (Nulls effects of isotropic components of capacitances)

$$\sum_{i=0}^{n-1} u_{ji} C_{oi} = 0, \text{ where } j = 0, 1, \ldots, m-1 \tag{24}$$

Restriction (ii) (Defines effect along measurement half-planes)

Let the weights $u_{ji}$ in equation (23) be given by:

$$u_{ji} = K_i \cos(2Mi - 2Dj) \tag{25}$$

where $K_i$, $i=0, 1, \ldots, n-1$ are weight factors applying to the $i^{th}$ electrode of the second electrode means. The angles $D_j$, where $j=0, 1, \ldots, m-1$ are angles from the reference half-plane to what we define as measurement half-planes. The measurement half-planes are all bounded by the test axis and intersect the wood surface, but otherwise the angles $D_j$ are arbitrary at this point in the development. The measurement half-planes should be considered as composites of the probing half-planes so that we can, by choosing the $u_{ji}$ values properly, effectively probe in whatever direction we please provided we have started with a good selection of probing half-planes. By substituting equation (25) into equations (24), the following useful restrictions are obtained.

$$\sum_{i=0}^{n-1} K_i C_{oi} \cos(2M_i - 2D_j) = 0, \text{ where } j = 0, 1, \ldots, m-1 \quad (26)$$

Some intuition about the meaning of the restrictions in equations (26) is possible. Let a 2-dimensional vector space be defined, and in it define n vectors where the $i^{th}$ vector $X_i$ has length $K_iC_{oi}$ and angle $2M_i$ with respect to a zero reference. Then, each of the m sums in equations (26) is seen to be the sum of all the projections of these vectors onto a line in the space at angle $2D_j$. If this is true of any arbitrary angle $2D_j$, then the vector sum of the n vectors in the space must be zero. Provided that any one of the n vectors can be written as a linear combination of the others, the factors $K_i$ can always be adjusted so that the vector sum is zero. Another restriction which ensures that all directions can be effectively probed by the measurement half-planes is that the vectors $X_i$, $i=0, 1, \ldots, n-1$ must span the 2-dimensional space. These restrictions are summarized as:

Restriction (iii) (Nulls effects of isotropic components of capacitances)

$$\sum_{i=0}^{n-1} X_i = 0 \quad (27)$$

Restriction (iv) (Dependence of the vectors $X_i$, $i=0, 1, \ldots n$)

For each vector $X_j$, $j=0, 1, \ldots n-1$, there exists a set of weights $a_{ji}$, $i=0, 1, \ldots, n-1$, and $i \neq j$, so that:

$$X_j = \sum_{\substack{i=0 \\ i \neq j}}^{n-1} a_{ji} X_i, j = 0, 1, \ldots, n-1 \quad (28)$$

Restriction (v) (Vectors $X_i$, $i=0, 1, \ldots, n-1$, span the 2-dimensional space)

For any vector $X$ in the 2-dimensional space, there exists a set of weights $a_i$, where $i=0,1,\ldots,n-1$, so that:

$$X = \sum_{i=0}^{n-1} a_i X_i \quad (29)$$

With Restriction (i) and the weights $u_{ji}$ defined as in equation (25), $V_j$ become:

$$V_j = \sum_{i=0}^{n-1} K_i C_{vi} \cos(2M_i - 2D_j)\cos(2M_i - 2G)$$

$$= \sum_{i=0}^{n-1} (K_i C_{vi}/2)\cos(2D_j - 2G) +$$

$$\sum_{i=0}^{n-1} (K_i C_{vi}/2)\cos(4M_i - 2D_j - 2G) \quad (30)$$

One can process the composite signals $V_j$ to obtain the grain angle G. As an example, let $n=3$ and $m=2$, $D_0=0$ degrees, $D_1=45$ degrees, and $M_i=i120$ degrees, with the isotropic and anisotropic components of capacitance being independent of i, that is, $C_{oi}=C_o$, and $C_{vi}=C_v$, where $i=0,1,2$. Then, by imposing restriction (i), the restrictions (ii) through (v) are satisfied, and further the second sum in equation (30) is zero. Also from equation (30), $V_0=(3C_v/2)\cos(2G)$ and $V_1=(3C_v/2)\sin(2G)$. Thus the "division" method, wherein G or a function of G can obtained from processing the quotient $V_1/V_0$, can be utilized. For geometries with isotropic capacitances $C_{oi}$ not all equal, for example if the second electrodes are not all of equal area or not at equal distances from the common first electrode, then the factors $K_i$ are adjusted until the products $K_iC_{oi}$ are all equal. In the case where time-varying electrical potential is applied to the common first electrode and signals are sensed at the second electrodes, the factors $K_i$ can be factors of amplifier gains; in the case where time-varying electrical potentials are applied to the second electrodes, the factors $K_i$ can be magnitude factors on driving potentials.

Another method would use the composite signals $V_j$ to amplitude modulate a time varying signal $F_j$, and then sum to obtain a resulting signal R.

$$R = \sum_{j=0}^{m-1} H_j V_j F_j \quad (31)$$

where $H_j$ is a weighting factor for the $j^{th}$ composite signal in the sum. The case where $F_j$ is a sinusoid with phase related to the angle of the measurement half-plane is particularly interesting. Let:

$$F_j = \cos(wt - 2D_j), \text{ where } j=0,1,\ldots,m-1 \quad (32)$$

where w is a scanning frequency appropriate for the particular application.

Then the resulting signal R, after substituting equations (30) and (32) into equation (31) and applying trigonometric identities, is:

$$R = \sum_{j=0}^{m-1} \sum_{i=0}^{n-1} (H_j k_i C_{vi}/4)\cos(wt-2G) \quad (33)$$

provided that the following restrictions are satisfied:

Restrictions (vi)

$$\sum_{i=0}^{n-1} (K_i C_{vi})\cos(4M_i) = 0, \quad (34)$$

and $$\sum_{j=0}^{m-1} H_j \cos(4D_j) = 0 \quad (35)$$

From equation (33), the grain angle G, or a desired function of G, is readily obtained with phase demodulation.

APPLICATION TO LUMBER STRENGTH ESTIMATION

The "tracks" strength estimation model (Bechtel and Allen, 1987) requires that grain angle measurements be made on multiple tracks or rows about the surface of each piece of lumber. This requires a means of making simultaneous measurements in these multiple tracks with several grain angle sensors. The simplicity of the newly discovered sensor geometry and processing methods lends itself well to a production-line multiple track arrangement.

There are difficulties in economically achieving real-time results when dealing with the quantities of data that are available for strength estimation purposes at production speeds. The tracks algorithm is well suited to our real-time requirement because it allows significant preprocessing steps to be performed. Multiple parallel microcontrollers and dedicated computational hardware further preprocess the grain angle data, thus greatly reducing the storage and speed requirements for the main processor. This makes real-time estimation of tensile strength possible and practical. Schematic views of the equipment needed are presented in FIGS. 18 and 19.

Each sensor 60 (FIG. 18) is located so that its electrode array is positioned in close proximity to the lumber surface 61. The RF drive signals are generated nearby in an oscillator drive circuit 62. Initial amplification and demodulation of the sensed signals will also occur nearby at circuits 63 to reduce noise pickup and avoid sending RF signals over a cable to the main processor location.

The component functions to the left of the dashed line 64 in FIG. 18 are located near the lumber cross-section. The sensors 60 are dispersed longitudinally so that they can be centered over their defined track positions about the top, sides and bottom of the lumber cross-section. Although the number N of sensors 60 is a variable, our present plan uses N=16.

The "tracks" strength estimation algorithm uses E measurements as well as grain angle measurements. For this purpose, E is Modulus of Elasticity (MOE), an important structural property of dimension lumber, determined from a measurement of its flatwise bending stiffness. The primary machine used in North American sawmills for measuring E is the CLT—Continuous Lumber Tester—jointly produced by Irvington-Moore, of Portland, Oreg., U.S.A. and Metriguard Inc of Pullman, Wash., U.S.A. As shown in FIG. 19, the grain angle measuring apparatus including sensors 60 is positioned at the outfeed of a CLT 70. Another clamp roll section 72, just as is used in the CLT, is provided at a distance of about 48 inches (1.22 m) downstream from the CLT outfeed clamp roll section 71. This clamp roll section 72 is mounted in a frame extension attached rigidly to the CLT frame so that the position of the lumber cross-section between the CLT outfeed at 71 and the additional clamp roll section 72 is well controlled.

The grain angle sensors 60 at the top face and along the edges of the lumber are fixed vertically with a resilient mounting arrangement and controlled horizontally so that sensor reference surfaces are located at a distance from the wood of about 0.100 inch (2.54 mm). A bridge structure slung between clamp roll sections supports and locates sensors 60 with controlled compliance at the bottom face of the lumber. The elevation of the bottom sensors 60 changes with the lower clamp rolls. Vertical and horizontal funnel guides (not shown) help protect the sensors from being struck by the lumber passing through.

An alternative location for the grain angle sensors 60 is within the CLT. This is a more desirable location because less modification of lumber handling apparatus is required.

Demodulated signals from the N sensors along with a phase synchronization signal are routed in separate wires from the sensors 60 to a common electronic cabinet containing the circuitry shown to the right of line 64 in FIG. 18. There, the track signals are processed by N track processors 67, one for each track. The track values from the N track processors 67 are combined in another circuit called the I/O combiner 68. Still another processor, the main processor 69, accepts as input from each cross-section, the modulus of elasticity E from the CLT and the combined result from the I/O combiner. The main processor 69 uses these inputs to estimate tensile strength. FIG. 18 illustrates these processing component connections.

In a commercial operational system, the main processor would use the tensile strength estimate and the E measurements to sort each piece of lumber into one of several categories.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

We claim:

1. A sensor for use in quantifying grain angle in wood, comprising:
    electrically conductive first and second electrode means for effecting capacitive coupling between them through an adjacent wood specimen to detect signals that are a function of grain angle in the wood specimen;
    the first electrode means comprising an electrode operative surface having a sensor axis; and
    the second electrode means comprising a plurality of electrode operative surfaces angularly arranged about the sensor axis;
    the operative surfaces of the second electrode means being spaced apart from one another and from the operative surface of the first electrode means.

2. The sensor of claim 1 wherein the operative surfaces of the second electrode means are arranged along an arcuate path centered on the sensor axis.

3. The sensor of claim 2 wherein the arcuate path fully encircles the sensor axis.

4. The sensor of claim 1 wherein the operative surfaces of the second electrode means are spaced at equal angle intervals about the sensor axis.

5. The sensor of claim 1, further comprising:
    a guard ring of electrically conductive material spaced radially outward from and surrounding the first and second electrode means.

6. The sensor of claim 1, further comprising:
    a guard ring of electrically conductive material interposed between and spaced apart from the first electrode means and the second electrode means.

7. The sensor of claim 1 wherein:
    the number of electrode operative surfaces comprising the second electrode means is an integer multiple of 2; and
    the electrode operative surfaces of the second electrode means are arranged as diametrically opposite pairs.

8. The sensor of claim 7 wherein the electrode operative surfaces of each diametrically opposite pair of surfaces are electrically wired together.

9. The sensor of claim 1 wherein:

one or more points on the operative surface of the first electrode means are located in a first plane that is perpendicular to the sensor axis; and one or more points on each operative surface of the second electrode means are located in a second plane that is parallel to the first plane and perpendicular to the sensor axis.

10. An apparatus for quantifying grain angle in wood, comprising:

electrically conductive first and second electrode means for effecting capacitive coupling between them through an adjacent wood specimen to detect signals that are functions of grain angle of the wood specimen;

the first electrode means comprising an electrode operative surface having a sensor axis;

the second electrode means comprising a plurality of electrode operative surfaces arranged about the sensor axis;

the operative surfaces of the second electrode means being spaced apart from one another and from the operative surface of the first electrode means;

drive circuit means operatively connected to one of the first or second electrode means for applying time varying electrical potentials to the wood specimen through the one electrode means;

sensing means operatively connected to the remaining one of the first and second electrode means for detecting signals through the remaining electrode means, resulting from capacitive coupling between the first and second electrode means and through the adjacent wood specimen; and processing means operatively connected to the sensing means for deriving a signal that is a function of grain angle in the wood specimen.

11. The apparatus of claim 10 wherein:

the operative surfaces of the second electrode means are arranged along an arcuate path centered about the sensor axis;

the arcuate path fully encircles the sensor axis; and the operative surfaces of the second electrode means are spaced at equal intervals along the arcuate path.

12. The apparatus of claim 11 further comprising a guard ring of electrically conductive material spaced radially outward and spaced apart from the first and second electrode means.

13. The apparatus of claim 11 further comprising a guard ring of electrically conductive material interposed between and spaced apart from the first electrode means and the second electrode means.

14. The apparatus of claim 11 wherein the second electrode means comprises eight electrode operative surfaces; and the electrode operative surfaces of diametrically opposite pairs are electrically wired together.

15. A method for determining grain angle in wood about a selected test axis, the test axis being substantially perpendicular to a surface of a wood specimen at a test point, grain angle being the angle having a magnitude less than or equal to 90 degrees from a reference half-plane with its boundary on the test axis to a wood fiber plane containing the test axis and parallel to the wood fibers in the vicinity of the test point, the method comprising the following steps:

obtaining a plurality of first signals, each first signal being a measure of permittivity in the vicinity of the test point and along a probing half-plane, the probing half-plane having the test axis as its boundary and intersecting both a common first area and one of a plurality of second areas on the wood surface, both areas being in the vicinity of the test point, the first signals being obtained by applying a time varying electrical potential to the wood specimen through the wood surface at the common first area and sensing the first signals at the second areas; and processing the first signals to derive a signal that is a function of the grain angle of the wood specimen in the vicinity of the test point.

16. The method of claim 15 wherein the plurality of second areas on the wood surface are arranged along an arcuate path centered at the test point.

17. The method of claim 15 wherein the probing half-planes are in pairs with each member of a pair being perpendicular to the other member of the pair.

18. The method of claim 17 wherein there are exactly two pairs of probing half-planes.

19. The method of claim 15 wherein there are exactly eight probing half-planes equiangularly positioned about the test axis.

20. The method of claim 15 wherein the number of probing half-planes is n, n being an integer greater than two, the $i^{th}$ probing half-plane being positioned at angle $M_i$ relative to the reference half-plane, with the following condition on the angles $M_i$, where $i=0,1,\ldots,n-1$:

in a two-dimensional vector space, any vector in the space can be written as a linear combination of n vectors $M_i$, where $i=0,1,\ldots,n-1$, the vector $X_i$ having unit length and angle $2M_i$, the angles all having a common reference, the vectors $X_i$ having the additional property that any one of them can be written as a linear combination of the others.

21. The method of claim 15 wherein the processing step includes the following substep:

forming a plurality of additional signals, each additional signal being a function of the first signals and having the additional property that it is independent of the isotropic component of permittivity in the vicinity of the test point, the additional signal being dependent on permittivity only through the anisotropic component of permittivity along a measurement half-plane chosen for that additional signal, all measurement half-plane boundaries being the test axis.

22. The method of claim 21 wherein the functions defining the additional signals are substantially linear.

23. The method of claim 15 wherein the processing step includes the following substep:

forming a plurality of additional signals, each additional signal being a sinusoid, the sinusoid being amplitude modulated by a signal that is dependent on permittivity in the vicinity of the test point only through the anisotropic component of permittivity along a measurement half-plane, all measurement half-plane boundaries being the test axis, the sinusoids all having a common frequency.

24. The method of claim 15 wherein the processing step includes the following substep:

combining a plurality of sinusoids to yield an additional signal, each sinusoid having been amplitude modulated by a signal depending on permittivity in the vicinity of the test point only through the anisotropic component of permittivity along a measurement half-plane, all measurement half-plane boundaries being the test axis, the sinusoids all having a common frequency, the additional signal being a sinusoid whose phase contains the grain angle information.

25. The method of claim 15 wherein the processing step includes phase demodulation.

26. The method of claim 15 wherein the processing step includes the following substeps:
   (1) forming a plurality of second signals, each second signal being a function of the first signals and having the additional property that it is dependent on permittivity in the vicinity of the test point only through the anisotropic component of permittivity along a measurement half-plane, all measurement half-plane boundaries being the test axis;
   (2) forming a plurality of third signals, each third signal being a sinusoid that has been amplitude modulated by one of the second signals, the sinusoids all having a common frequency;
   (3) combining the third signals to obtain a fourth signal, the fourth signal being a sinusoid whose phase is twice the grain angle plus a known constant offset;
   (4) phase demodulating, level shifting, and amplitude scaling the fourth signal to obtain grain angle.

27. The method of claim 26 wherein:
the number of probing half-planes is n, n being an integer greater than two, the $i^{th}$ probing half-plane being positioned at angle $M_i$ relative to the reference half-plane, where $i=0,1,\ldots,n-1$;
the number of measurement half-planes and hence second signals formed is m, m being an integer greater than one, the $j^{th}$ measurement half-plane being positioned at angle $D_j$ relative to the reference half-plane, $j=0,1,\ldots,m-1$, the second signals $V_j$, $j=0,1,\ldots,m-1$, being given by weighted sums of first signals $S_i$, where $i=0,1,\ldots,n-1$, as follows:

$$V_j = \sum_{i=0}^{n-1} [S_i K_i \cos(2M_i - 2D_j)],$$

where $j=0,1,\ldots,m-1$, where $K_i\cos(2M_i-2D_j)$, $i=0,1,\ldots,n-1$, are the weighting factors applied to the first signals $S_i$, where $i=0,1,\ldots,n-1$, in the weighted sum for the $j^{th}$ second signal $V_j$, and the factors $K_i$, $i=0,1,\ldots,n-1$, are chosen so that each $V_j$ is dependent on permittivity in the vicinity of the test point only through the anisotropic component of permittivity along the $j^{th}$ measurement half-plane;
the third signals $F_j$, where $j=0,1,\ldots,m-1$, are amplitude modulated sinusoids given by:

$$F_j = V_j \cos(wt - 2D_j), \text{ where } j=0,1,\ldots,m-1,$$

where w is the common frequency, and t is a running time variable; and
the combining operation to yield the fourth signal R is weighted summation, R being given by:

$$R = \sum_{j=0}^{m-1} H_j F_j$$

where $H_j$ is the weight for the jth component of the sum.

28. The method of claim 27 wherein:
the plurality of second areas on the wood surface is arranged along an arcuate path centered at the test point;
the angles from the reference half-plane to the probing half-planes are either $M_i = i360/n$ or $M_i = i180/n$ degrees, where $i=0,1,\ldots,n-1$;
the angles from the reference half-plane to the remaining measurement half-planes are $D_j = j90/m$ degrees, where $j=0,1,\ldots,m-1$;
the factors $K_i$, $i=0,1,\ldots,n-1$, are all equal to one; and the weights $H_j$, $j=0,1,\ldots,m-1$, are all equal to one.

29. The method of claim 28 where n=8, m=2, and $M_i = i45$ degrees, where $i=0,1,\ldots,n-1$.

30. The method of claim 15 wherein the processing step includes the following substeps:
   (1) forming a plurality of second signals, each second signal being a function of the first signals and having the additional property that it is dependent on permittivity in the vicinity of the test point only through the anisotropic component of permittivity along a measurement half-plane, all measurement half-plane boundaries being the test axis;
   (2) dividing one second signal by another to obtain a known function of grain angle;
   (3) solving the known functional relationship of substep (2) to obtain grain angle or other desired function of grain angle.

31. The method of claim 30 wherein:
the number of probing half-planes is n, n being an integer greater than two, the $i^{th}$ probing half-plane being positioned at angle $M_i$ relative to the reference half-plane, where $i=0,1,\ldots,n-1$; and
the number of measurement half-planes and hence second signals formed is m, m being an integer greater than one, the $j^{th}$ measurement half-plane being positioned at angle $D_j$ relative to the reference half-plane, where $j=0,1,\ldots,m-1$, the second signals $V_j$, where $j=0,1,\ldots,m-1$, being given by weighted sums of first signals $S_i$, where $i=0,1,\ldots,n-1$, as follows:

$$V_j = \sum_{i=0}^{n-1} [S_i K_i \cos(2M_i - 2D_j)],$$

where $j=0,1,\ldots,m-1$, where $K_i\cos(2M_i-2D_j)$ is the weighting factor applied to the first signal $S_i$ in this weighted sum for the $j^{th}$ second signal $V_j$, and the factors $K_i$, where $i=0,1,\ldots,n-1$, are chosen so that each $V_j$ is dependent on permittivity in the vicinity of the test point only through the anisotropic component of permittivity along the $j^{th}$ measurement half-plane.

32. The method of claim 31 wherein:
the plurality of second areas on the wood surface is arranged along an arcuate path centered at the test point;
the angles from the reference half-plane to the probing half-planes are either $M_i = i360/n$ or $M_i = i180/n$ degrees, where $i=0,1,\ldots,n-1$;
the angles from the reference half-plane to the measurement half-planes are $D_j = j90/m$ degrees, where $j=0,1,\ldots,m-1$;
the factors $K_i$, where $i=0,1,\ldots,n-1$, are all equal to one; and
the weights $H_j$, where $j=0,1,\ldots,m-1$, are all equal to one.

33. The method of claim 32 where n=8, m=2, and $M_i = i45$ degrees, and where $i=0,1,\ldots,n-1$.

34. A method for determining grain angle in wood about a selected test axis, the test axis being substantially perpendicular to a surface of a wood specimen at a test point, grain angle being the angle having a magnitude less than or equal to 90 degrees measured from a reference half-plane to a wood fiber plane, the reference half-plane having the test axis as its boundary, the wood fiber plane containing the test axis and being parallel to the wood fibers in the vicinity of the test point, the method comprising the following steps:

obtaining one or more second signals, each second signal being inherently a combination of first signals, each first signal being a function of permittivity in the vicinity of the test point and along a probing half-plane, the probing half-plane having the test axis as its boundary and intersecting both a common first area and one of a plurality of second areas on the wood surface, both areas being in the vicinity of the test point, the second signals being obtained by applying time varying electrical potentials to the wood specimen through the wood surface at the second areas and sensing the second signals at the common first area;

processing the second signals to derive a signal that is a function of the grain angle of the wood specimen in the vicinity of the test point.

35. The method of claim 34 wherein the plurality of second areas on the wood surface are arranged along an arcuate path centered at the test point.

36. The method of claim 34 wherein the probing half-planes are in pairs with each member of a pair being perpendicular to the other member of the pair.

37. The method of claim 34 wherein there are two pairs of probing half-planes.

38. The method of claim 34 wherein there are eight probing half-planes equiangularly positioned about the test axis.

39. The method of claim 34 wherein the geometry and locations of the first and second areas and the time varying electrical potentials applied to the second areas are designed so that each second signal has the additional property that it is independent of the isotropic component of permittivity in the vicinity of the test point, the second signal being dependent on permittivity only through the anisotropic component of permittivity along a measurement half-plane chosen for that second signal, all measurement half-plane boundaries being the test axis.

40. The method of claim 34 wherein:
the step of applying time-varying electrical potentials to the wood specimen through the wood surface at the second areas includes the following substep:
applying time varying electrical potentials to a pair of the second areas, the potential to one second area of the pair being equal in magnitude and opposite in polarity to the potential applied to the other second area of the pair, the second areas being intersected by a pair of probing half-planes that are orthogonal to one another.

41. The method of claim 34 wherein:
the step of applying time-varying electrical potentials to the wood specimen through the wood surface at the second areas includes the following condition:
the time varying electrical potentials applied to the second areas satisfy:

$$\sum_{i=0}^{n-1} C_{oi}P_i = 0$$

where
n is the number of second areas,
$P_i$ is the time varying electrical potential applied to the $i^{th}$ second area,
$C_{oi}$ is a weighting constant proportional to the isotropic component of capacitance between the $i^{th}$ second area and the common first area, the isotropic component of capacitance being the capacitance in the absence of the anisotropic component of permittivity in the wood.

42. The method of claim 34 wherein:
the number of probing half-planes is n, n being an integer greater than two, the $i^{th}$ probing half-plane being positioned at angle $M_i$ relative to the reference half-plane, where $i=0,1,\ldots,n-1$;
the time varying electrical potential applied to the wood specimen through the wood surface at the $i^{th}$ second area is $P_i$ given by $P_i=K_i(\cos(-2M_i-2D))f(t)$, where $i=0,1,\ldots,n-1$, where $K_i$ is a multiplying factor, 2D is an arbitrary phase, and f(t) is a time varying component of the potential chosen so as to best probe the wood; and
the angles $M_i$ and the time varying electrical potentials $P_i$, where $i=0,1,\ldots,n-1$, satisfy the conditions:

$$\sum_{i=0}^{n-1} C_{oi}P_i = 0, \tag{1}$$

for all values of phase 2D,
where:
$C_{oi}$ is the isotropic component of capacitance between the $i^{th}$ second area and the common first area, the isotropic component of capacitance being the capacitance in the absence of the anisotropic component of permittivity in the wood, and (2) in a two-dimensional vector space, any vector in the space can be written as a linear combination of n vectors $X_i$, $i=0,1,\ldots,n-1$, the vector $X_i$ having unit length and angle $2M_i$, the angles all having a common reference, the vectors $X_i$ having the additional property that any one of them can be written as a linear combination of the others.

43. The method of claim 42 wherein:
the phase 2D is given by $2D=w_c t$ and $f(t)=1$ where $w_c$ is a carrier frequency chosen to best probe the wood specimen, and t is a running time variable; and
the processing step includes phase demodulation at the carrier frequency $w_c$.

44. The method of claim 42 wherein:
the phase 2D is given by $2D=w_m t$ and $f(t)=\cos(w_c t)$, where $w_m$ is a subcarrier frequency, $w_c$ is a carrier frequency chosen to best probe the wood, and t is a running time variable; and
the processing step includes phase demodulation at the subcarrier frequency $w_m$.

45. The method of claim 34 wherein:
the number of probing half-planes is 8, the $i^{th}$ probing half-plane being positioned at angle i45 degrees relative to the reference half-plane, where i=0,1, ..,7;

the time varying electrical potential applied to the wood specimen through the wood surface at the $i^{th}$ second area is $P_i$ given by $P_i = K\cos(i90 - w_c t)$, where i=0,1,...,7, where K is an amplitude factor, $w_c$ is a frequency chosen so as to probe the wood for its permittivity properties, and t is a running time variable; and the processing step for the second signal sensed at the common first area includes phase demodulation.

46. The method of claim 34 wherein:

the number of probing half-planes is 8, the $i^{th}$ probing half-plane being positioned at angle i45 degrees relative to the reference half-plane, where i=0,1, ..,7;

the time varying electrical potential applied to the wood specimen through the wood surface at the $i^{th}$ second area is $P_i$ given by $P_i = K(\cos(i90-w_m t))(\cos w_c t)$, where i=0,1,...,7, where K is an amplitude factor, $w_c$ is a frequency chosen so as to probe the wood for its permittivity properties, $w_m$ is a subcarrier frequency chosen for scanning the wood surface, and t is running time variable; and the processing step for the second signal sensed at the common first area includes phase demodulation.

47. The method of claim 34 wherein:

the time-varying electrical potentials are applied to the wood specimen through the wood surface at the second areas; and a plurality of second signals are sensed at the common first area, one second signal during each time interval of a plurality of time intervals, the plurality of second signals being stored for further processing.

48. The method of claim 47 wherein the further processing includes dividing one stored second signal by another to get a known function of grain angle.

49. The method of claim 34 wherein:

the plurality of second areas on the wood surface is arranged along an arcuate path centered at the test point;

the number of second areas is an integer multiple of four;

the step of applying time-varying electrical potentials to the wood specimen through the wood surface at the second areas includes the following substeps:

(1) during a first period of time, applying time varying electrical potentials to a first pair of the second areas, the potential applied to one second area of the pair being equal in magnitude and opposite in polarity from the potential applied to the other second area of the pair, the areas of the first pair being intersected by a first pair of probing half-planes that are orthogonal to one another;

(2) during a second period of time, applying time varying electrical potentials to a second pair of the second areas, the potential applied to one second area of the pair being equal in magnitude and opposite in polarity from the potential applied to the other second area of the pair, the areas of the second pair being intersected by a second pair of probing half-planes that are orthogonal to one another, and are respectively offset 45 degrees in a common direction from the corresponding probing half-planes of the first pair of second areas.

* * * * *

UNITED STATES PATENT AND TRADEMARK OFFICE
CERTIFICATE OF CORRECTION

PATENT NO.  : 4,972,154

DATED       : November 20, 1990

INVENTOR(S) : Friend K. Bechtel et al.

It is certified that error appears in the above-identified patent and that said Letters Patent is hereby corrected as shown below:

Column 10, line 58 -- delete the hyphen (-) at the end of the line.

Column 10, line 65 -- delete "$c_o$ and $c_v$" and substitute --$C_o$ and $C_v$--.

Column 11, line 52 -- delete the hyphen (-) at the end of the line.

Column 11, line 55 -- delete the hyphen (-) at the end of the line.

Column 12, line 7 -- delete the hyphen (-) at the end of the line.

Column 13, line 45 -- change "$c_v$" to --$C_v$--.

Column 14, line 3 -- change "and s" and substitute --and 5--.

Column 14, line 20 -- delete "(3c)" and substitute --(3b)--.

UNITED STATES PATENT AND TRADEMARK OFFICE
CERTIFICATE OF CORRECTION

PATENT NO. : 4,972,154

DATED : November 20, 1990

INVENTOR(S) : Friend K. Bechtel et al.

It is certified that error appears in the above-identified patent and that said Letters Patent is hereby corrected as shown below:

Column 14, line 35 -- delete the two lines of formulas as printed and substitute the following:

$$2e_B(t) - (1/C_{45})\int_0^t i(u)du - (1/C_{135})\int_0^t i(u)du = 0$$

$$e_s(t) = e_B(t) - (1/C_{45})\int_0^t i(u)du$$

Column 14, line 54 -- change "(3b)" to --(3c)--.

Column 15, line 18 -- change "S" to --5--.

Column 16, line 35 -- delete the two lines of formulas as printed and substitute the following:

$$g(t) = (1/T)\int_{t-T}^t f_m(u)e^2c(u)du$$

$$= (1/T)f_m(t)\int_{t-T}^t e^2c(u)du$$

UNITED STATES PATENT AND TRADEMARK OFFICE
CERTIFICATE OF CORRECTION

PATENT NO. : 4,972,154

DATED : November 20, 1990

INVENTOR(S) : Friend K. Bechtel et al.

It is certified that error appears in the above-identified patent and that said Letters Patent is hereby corrected as shown below:

Column 16, after line 46 -- please delete the formula as printed and substitute the following:
$$f_m(t) = Qg(t)$$

Column 16, line 60 -- delete the formula as printed and substitute the following:
$$g(t) = (1/z)\int_{-\infty}^{t} f_m(u)e^2c(u)\exp(-(t-u)/z)du$$

Column 17, line 5 -- delete the formula as printed and substitute the following:
$$f_m(t) = Qg(t)$$

Column 17, after line 25 -- a table of formulas should be presented as follows:

| Electrodes | Drive Voltage | | |
|---|---|---|---|
| 0,4 | $e_{04}(t)$ | = | $e_c(t)$ |
| 1,5 | $e_{15}(t)$ | = | $e_c(t-T/4)$ |
| 2,6 | $e_{26}(t)$ | = | $e_c(t-T/2)$ |
| 3,7 | $e_{37}(t)$ | = | $e_c(t-3T/4)$ |

(11)

UNITED STATES PATENT AND TRADEMARK OFFICE

CERTIFICATE OF CORRECTION

PATENT NO. : 4,972,154

DATED : November 20, 1990

INVENTOR(S) : Friend K. Bechtel et al.

It is certified that error appears in the above-identified patent and that said Letters Patent is hereby corrected as shown below:

Column 17, line 60 -- delete the three lines of formula as printed and substitute the following:

$$\begin{aligned} e_s(t) &= (C_v/Co)(\cos(2G-45)\cos(w_c t-45) \\ &\quad + \sin(2G-45)\sin(w_c t-45)) \\ &= (C_v/Co)\cos(w_c t-2G) \end{aligned}$$

(13)

Column 18, line 5 -- delete the equations as printed and substitute the following:

$$e_c(t) = \begin{cases} +1, & nT \le t < T/2 + nT \\ -1, & T/2 + nT \le t < (n+1)T \end{cases}$$

(14)

UNITED STATES PATENT AND TRADEMARK OFFICE

CERTIFICATE OF CORRECTION

PATENT NO.    : 4,972,154

DATED         : November 20, 1990

INVENTOR(S)   : Friend K. Bechtel et al.

It is certified that error appears in the above-identified patent and that said Letters Patent is hereby corrected as shown below:

Column 18, line 20 -- delete the table of equations as printed and substitute the following:

| Time Interval | Positive Electrodes | Negative Electrodes |
|---|---|---|
| $0 \leq t < T/4$ | 0, 4, 3, 7 | 1, 5, 2, 6 |
| $T/4 \leq t < T/2$ | 0, 4, 1, 5 | 2, 6, 3, 7 |
| $T/2 \leq t < 3T/4$ | 1, 5, 2, 6 | 0, 4, 3, 7 |
| $3T/4 \leq t < T$ | 2, 6, 3, 7 | 0, 4, 1, 5 |

(15)

Column 18, after line 30 -- delete the table of equations as printed and substitute the following:

| Time Interval | Sense Electrode Signal, $e_s(t)$ | | |
|---|---|---|---|
| $0 \leq t < T/4$ | $(C_v/C_o)\cos 2G$ | $= C_v/C_o \, \cos(w_c t - 2G)\|$ | $t=0$ |
| $T/4 \leq t < T/2$ | $(C_v/C_o)\sin 2G$ | $= C_v/C_o \, \cos(w_c t - 2G)\|$ | $t=T/4$ |
| $T/2 \leq t < 3T/4$ | $-(C_v/C_o)\cos 2G$ | $= C_v/C_o \, \cos(w_c t - 2G)\|$ | $t=T/2$ |
| $3T/4 \leq t < T$ | $-(C_v/C_o)\sin 2G$ | $= C_v/C_o \, \cos(w_c t - 2G)\|$ | $t=3T/4$ |

(16)

UNITED STATES PATENT AND TRADEMARK OFFICE

CERTIFICATE OF CORRECTION

PATENT NO. : 4,972,154

DATED : November 20, 1990

INVENTOR(S) : Friend K. Bechtel et al.

It is certified that error appears in the above-identified patent and that said Letters Patent is hereby corrected as shown below:

Column 19, line 1 -- delete the table of formulas as printed and substitute the following:

| Electrodes | Drive Voltage | |
|---|---|---|
| 0,4 | $e_{04}(t) = e_m(t) e_c(t)$ | |
| 1,5 | $e_{15}(t) = e_m(t - T_m/4) e_c(t)$ | |
| 2,6 | $e_{26}(t) = e_m(t - T_m/2) e_c(t)$ | |
| 3,7 | $e_{37}(t) = e_m(t - 3T_m/4) e_c(t)$ | (17) |

Column 20, line 13 -- change "AB" to --A$\underline{B}$--.

Column 20, line 14 -- change "AB" to --A$\underline{B}$--.

Column 20, line 16 -- change "AB" to --A$\underline{B}$--.

Column 20, line 17 -- change "EC" to --$\underline{EC}$--.

Column 20, line 25 -- change "ECM" to --$\underline{ECM}$--.

UNITED STATES PATENT AND TRADEMARK OFFICE
CERTIFICATE OF CORRECTION

PATENT NO. : 4,972,154

DATED : November 20, 1990

INVENTOR(S) : Friend K. Bechtel et al.

It is certified that error appears in the above-identified patent and that said Letters Patent is hereby corrected as shown below:

Column 20, line 41 -- change "AB" to --A$\underline{B}$--.

Column 23, line 15 -- cancel "difference" and substitute --differences--.

Column 23, line 38 -- cancel "control" and substitute --controls--.

Column 26, line 2 -- cancel "$c_i$" and substitute --$C_i$--.

Column 27, line 27 -- delete the equation as printed and substitute the following:

$$\sum_{i=0}^{n-1} \underline{x}_i = \underline{0} \tag{27}$$

Column 27, line 31 -- change "$X_i$" to --$\underline{X}_i$--.

Column 27, line 34 -- change "$X_j$" to --$\underline{X}_j$--.

UNITED STATES PATENT AND TRADEMARK OFFICE
CERTIFICATE OF CORRECTION

PATENT NO. : 4,972,154

DATED : November 20, 1990

INVENTOR(S) : Friend K. Bechtel et al.

It is certified that error appears in the above-identified patent and that said Letters Patent is hereby corrected as shown below:

Column 27, after line 35 -- delete the formula as printed and substitute the following:

$$X = \sum_{i=0}^{n-1} a_i \underline{X_i} \qquad (28)$$

Column 27, line 41 -- change "$X_i$" to --$\underline{X_i}$--.

Column 27, line 43 -- "X" to --$\underline{X}$--.

Column 27, after line 45 -- delete the formula as printed and substitute the following:

$$X = \sum_{i=0}^{n-1} a_i \underline{X_i} \qquad (29)$$

Column 28, line 3 -- delete the formula as printed and substitute the following --$V_1 = (3C_v/2)\sin(2G)$--.

UNITED STATES PATENT AND TRADEMARK OFFICE
CERTIFICATE OF CORRECTION

PATENT NO. : 4,972,154

DATED : November 20, 1990

INVENTOR(S) : Friend K. Bechtel et al.

It is certified that error appears in the above-identified patent and that said Letters Patent is hereby corrected as shown below:

Column 28, line 33 -- delete the formula as printed and substitute the following:

$$R = \sum_{j=0}^{m-1} \sum_{i=0}^{n-1} (H_j K_i C_{vi}/4)\cos(wt - 2G) \tag{33}$$

Column 32, line 30 -- change "$M_i$" to --$\underline{X}_i$--.

Column 32, line 30 -- change "$X_i$" (at the end of the line) to --$\underline{X}_i$--.

Column 32, line 32 -- change "$X_i$" to --$\underline{X}_i$--.

Column 33, line 40 -- delete the formula as printed and substitute the following:

$$V_j = \sum_{i=0}^{n-1} [S_i K_i \cos(2M_i - 2D_j)], \text{ where } j=0,1,\ldots,m-1,$$

UNITED STATES PATENT AND TRADEMARK OFFICE
CERTIFICATE OF CORRECTION

PATENT NO. : 4,972,154        Page 10 of 11

DATED : November 20, 1990

INVENTOR(S) : Friend K. Bechtel et al.

It is certified that error appears in the above-identified patent and that said Letters Patent is hereby corrected as shown below:

Column 33, line 42 -- delete the entire line.

Column 34, line 40 -- delete the formula as printed and substitute the following:

$$V_j = \sum_{i=0}^{n-1} [S_i K_i \cos(2M_i - 2D_j)], \text{ where } j=0,1,...,m-1,$$

Column 34, line 45 -- delete the entire line.

Column 35, line 8 -- change "paralle" to --parallel--.

Column 36, line 8 -- should be rewritten to read: --the $i^{th}$ second area,--.

Column 36, line 9 -- delete the entire line.

Column 36, line 24 -- delete the hyphen (-) at the end of the line.

UNITED STATES PATENT AND TRADEMARK OFFICE
CERTIFICATE OF CORRECTION

PATENT NO.    : 4,972,154

DATED         : November 20, 1990

INVENTOR(S)   : Friend K. Bechtel et al.

It is certified that error appears in the above-identified patent and that said Letters Patent is hereby corrected as shown below:

Column 36, line 35 -- delete the presentation of the formula and substitute the following:

(1) $$\sum_{i=0}^{n-1} C_{0i} P_i = 0, \textit{ for all values of phase 2D}$$

Column 36, line 37 -- delete the entire line (reading "for all values of phase 2D,").

Column 36, line 47 -- change "$X_i$" (both occurrences) to --$\underline{X}_i$--.

Column 36, line 49 -- change "$X_i$" to --$\underline{X}_i$--.

Signed and Sealed this

Nineteenth Day of May, 1992

Attest:

DOUGLAS B. COMER

Attesting Officer     Acting Commissioner of Patents and Trademarks

UNITED STATES PATENT AND TRADEMARK OFFICE
CERTIFICATE OF CORRECTION

PATENT NO. : 4,972,154

DATED : November 20, 1990

INVENTOR(S) : Friend K. Bechtel et al.

It is certified that error appears in the above-identified patent and that said Letters Patent is hereby corrected as shown below:

Column 16, line 35 -- delete the two lines of formulas as printed and substitute the following:

$$g(t) = (1/T)\int_{t-T}^{t} f_m(u)e_c^2(u)du$$

$$= (1/T)f_m(t)\int_{t-T}^{t} e_c^2(u)du$$

Column 16, line 60 -- delete the formula as printed and substitute the following:

$$g(t) = (1/z)\int_{-\infty}^{t} f_m(u)e_c^2(u)\exp(-(t-u)/z)du$$

Column 27, after line 35 -- delete the formula as printed and substitute the following:

$$Xj = \sum_{\substack{i=0 \\ i \neq j}}^{n-1} a_{ji} X_i, \; j=0,1,\ldots, n-1$$

UNITED STATES PATENT AND TRADEMARK OFFICE
CERTIFICATE OF CORRECTION

PATENT NO. : 4,972,154

DATED : November 20, 1990

INVENTOR(S) : Friend K. Bechtel et al.

It is certified that error appears in the above-identified patent and that said Letters Patent is hereby corrected as shown below:

Column 27, after line 45 -- delete the formula as printed and substitute the following:

$$\underline{X} = \sum_{i=0}^{n-1} a_i X_i$$

Signed and Sealed this

Twenty-first Day of September, 1993

*Attest:*

BRUCE LEHMAN

*Attesting Officer*     *Commissioner of Patents and Trademarks*